US008507651B2

(12) United States Patent
Bar-Or

(10) Patent No.: US 8,507,651 B2
(45) Date of Patent: Aug. 13, 2013

(54) TREATMENT OF DISEASES AND CONDITIONS MEDIATED BY INCREASED PHOSPHORYLATION

(75) Inventor: David Bar-Or, Englewood, CO (US)

(73) Assignee: DMI Acquisition Corp., Greenwood Village, CO (US)

(*) Notice: Subject to any disclaimer, the term of this patent is extended or adjusted under 35 U.S.C. 154(b) by 0 days.

(21) Appl. No.: 13/152,072

(22) Filed: Jun. 2, 2011

(65) Prior Publication Data
US 2011/0230417 A1 Sep. 22, 2011

Related U.S. Application Data

(62) Division of application No. 10/723,247, filed on Nov. 25, 2003, now Pat. No. 7,982,008.

(60) Provisional application No. 60/429,924, filed on Nov. 27, 2002.

(51) Int. Cl.
A61K 38/16 (2006.01)
A61K 38/00 (2006.01)

(52) U.S. Cl.
USPC .......... 530/352; 530/300; 514/1.1; 424/278.1

(58) Field of Classification Search
None
See application file for complete search history.

(56) References Cited

U.S. PATENT DOCUMENTS

| 3,558,770 A | 1/1971 | Gordon et al. |
|---|---|---|
| 3,901,979 A | 8/1975 | Nagasawa et al. |
| 3,941,763 A | 3/1976 | Sarantakis |
| 3,966,915 A | 6/1976 | Caprino et al. |
| 3,995,070 A | 11/1976 | Nagasawa et al. |
| 4,284,623 A | 8/1981 | Beck |
| 4,358,465 A | 11/1982 | Brule et al. |
| 4,419,369 A | 12/1983 | Nichols et al. |
| 4,454,338 A | 6/1984 | Fujii et al. |
| 4,462,990 A | 7/1984 | Jolles et al. |
| 4,612,122 A | 9/1986 | Ambrus et al. |
| 4,768,824 A | 9/1988 | Andonian |
| 4,777,243 A | 10/1988 | Jolles et al. |
| 4,798,824 A | 1/1989 | Belzer et al. |
| 4,847,283 A | 7/1989 | Harendza-Harinxma |
| 4,873,230 A | 10/1989 | Belzer et al. |
| 4,879,283 A | 11/1989 | Belzer et al. |
| 5,032,374 A | 7/1991 | Pastor et al. |
| 5,032,384 A | 7/1991 | Yeh et al. |
| 5,043,183 A | 8/1991 | Gershon et al. |
| 5,068,118 A | 11/1991 | Strandholm |
| 5,130,123 A | 7/1992 | Reynolds et al. |
| 5,141,957 A | 8/1992 | Jiang et al. |
| 5,180,578 A | 1/1993 | Gaffar et al. |
| 5,186,479 A | 2/1993 | Flowers |
| 5,189,046 A | 2/1993 | Burch et al. |
| 5,198,220 A | 3/1993 | Damani |
| 5,204,370 A | 4/1993 | Jiang et al. |
| 5,216,014 A | 6/1993 | Jiang et al. |
| 5,242,910 A | 9/1993 | Damanj |
| 5,270,310 A | 12/1993 | Bell et al. |
| 5,279,814 A | 1/1994 | Wuelknitz et al. |
| 5,286,479 A | 2/1994 | Garlich et al. |
| 5,289,479 A | 2/1994 | Oka et al. |
| 5,292,737 A | 3/1994 | Defauw |
| 5,298,237 A | 3/1994 | Fine |
| 5,302,375 A | 4/1994 | Viscio |
| 5,312,626 A | 5/1994 | Gergely et al. |
| 5,328,682 A | 7/1994 | Pullen et al. |
| 5,334,408 A | 8/1994 | Brule et al. |
| 5,344,841 A | 9/1994 | Jiang et al. |
| 5,352,476 A | 10/1994 | Brule et al. |
| 5,385,915 A | 1/1995 | Buxbaum et al. |
| 5,407,664 A | 4/1995 | Konopa |
| 5,432,198 A | 7/1995 | Jagdmann, Jr. |
| 5,466,437 A | 11/1995 | Gaffar et al. |
| 5,476,647 A | 12/1995 | Chow et al. |
| 5,514,536 A | 5/1996 | Taylor |
| 5,583,221 A | 12/1996 | Hu et al. |
| 5,622,699 A | 4/1997 | Ruoslahti et al. |
| 5,622,984 A | 4/1997 | Nakai et al. |
| 5,665,868 A | 9/1997 | Ramadoss et al. |
| 5,707,610 A | 1/1998 | Ibsen et al. |
| 5,709,873 A | 1/1998 | Bar-Shalom et al. |
| 5,710,172 A | 1/1998 | Kukreja et al. |
| 5,712,250 A | 1/1998 | Mukerji et al. |
| 5,738,840 A | 4/1998 | Richter |
| 5,739,407 A | 4/1998 | Bergstrom et al. |

(Continued)

FOREIGN PATENT DOCUMENTS

| EP | 471396 | 2/1992 |
|---|---|---|
| EP | 0699444 | 3/1996 |

(Continued)

OTHER PUBLICATIONS

Article (2011, updated) Other neoplasms, www.mrcophth.com/pathology/skin/otherlesions.html, pp. 1-4.*
Chen et al. (2005) Sites on phospholipase D2 phosphorylated by PKCa, Biochem. Biophy. Res. Comm., vol. 333, pp. 1322-1326.*
DermNet NZ (2011, updated) "Treatment of atopic dermatitis", www.dermnetnz.org/ dermatitis/treatment.html, pp. 1-5.*
"List of incurable diseases" (2011, updated) http://www.lumrix.net/health/List_of_incurable_diseases.html, pp. 1-3.*
Campbell et al., "Recombinant guinea pig and human RANTES activate macrophages but not eosinophils in the guinea pig," The Journal of Immunology, 1997, vol. 159(3), pp. 1482-1489.
Ferreira et al., "New aspects of the mode of action of nonsteroid anti-inflammatory drugs." Annual Review of Pharmacology, Apr. 1974, vol. 14, pp. 57-73.
Masaracchia et al., "Histone 4 Phosphotransferase Whole Activities in Proliferating Lymphocytes." The Journal of Biological Chemistry, 1977, vol. 252(20), pp. 7109-7117.

(Continued)

Primary Examiner — Manjunath Rao
Assistant Examiner — Samuel Liu
(74) Attorney, Agent, or Firm — Sheridan Ross P.C.

(57) ABSTRACT

The invention provides methods for the treatment of diseases and conditions mediated by increased phosphorylation, such as inflammation and cancer. The invention also provides methods for the inhibition of increased phosphorylation in cells, tissues and organs. The methods utilize a phosphate acceptor compound (PAC). The invention also provides products comprising a PAC.

4 Claims, 1 Drawing Sheet

(56) References Cited

U.S. PATENT DOCUMENTS

| | | | |
|---|---|---|---|
| 5,753,227 A | 5/1998 | Strahilevitz | |
| 5,785,887 A | 7/1998 | Steltenkamp et al. | |
| 5,786,335 A | 7/1998 | Cody et al. | |
| 5,795,611 A | 8/1998 | Slattery | |
| 5,817,295 A | 10/1998 | Chaudhari et al. | |
| 5,833,953 A | 11/1998 | Berrocal et al. | |
| 5,855,872 A | 1/1999 | Libin | |
| 5,858,332 A | 1/1999 | Jensen et al. | |
| 5,858,408 A | 1/1999 | Sotani et al. | |
| 5,861,156 A | 1/1999 | George et al. | |
| 5,863,202 A | 1/1999 | Fontenot et al. | |
| 5,869,095 A | 2/1999 | Gergely et al. | |
| 5,876,701 A | 3/1999 | Wong et al. | |
| 5,891,453 A | 4/1999 | Sagel et al. | |
| 5,902,786 A | 5/1999 | Bregman | |
| 5,906,811 A | 5/1999 | Hersh | |
| 5,916,548 A | 6/1999 | Hutchins et al. | |
| 5,922,307 A | 7/1999 | Montgomery | |
| 5,922,331 A | 7/1999 | Mausner | |
| 5,932,191 A | 8/1999 | Chevallier et al. | |
| 5,932,193 A | 8/1999 | Lopez et al. | |
| 5,932,580 A | 8/1999 | Levitzki et al. | |
| 5,942,254 A | 8/1999 | Mukerji et al. | |
| 5,942,274 A | 8/1999 | Slattery | |
| 5,945,418 A | 8/1999 | Bemis et al. | |
| 5,951,966 A | 9/1999 | Wang | |
| 5,952,295 A | 9/1999 | Arnaud-Battandier et al. | |
| 5,967,155 A | 10/1999 | Marcon | |
| 5,972,366 A | 10/1999 | Haynes et al. | |
| 5,976,507 A | 11/1999 | Wong et al. | |
| 5,980,249 A | 11/1999 | Fontenot et al. | |
| 6,026,829 A | 2/2000 | Mitha et al. | |
| 6,039,946 A | 3/2000 | Strahilevitz | |
| 6,045,780 A | 4/2000 | Bixler et al. | |
| 6,060,078 A | 5/2000 | Lee | |
| 6,066,673 A | 5/2000 | McIver et al. | |
| 6,071,412 A | 6/2000 | Ambrus et al. | |
| 6,080,481 A | 6/2000 | Ochs et al. | |
| 6,093,742 A | 7/2000 | Salituro et al. | |
| 6,102,050 A | 8/2000 | Marcon | |
| 6,146,661 A | 11/2000 | Hoshino | |
| 6,147,080 A | 11/2000 | Bemis et al. | |
| 6,190,724 B1 | 2/2001 | Sawatzki et al. | |
| 6,197,331 B1 | 3/2001 | Lerner et al. | |
| 6,228,347 B1 | 5/2001 | Hersh | |
| 6,232,094 B1 | 5/2001 | Hansson et al. | |
| 6,242,253 B1 | 6/2001 | Karin et al. | |
| 6,251,372 B1 | 6/2001 | Witt et al. | |
| 6,264,623 B1 | 7/2001 | Strahilevitz | |
| 6,268,194 B1 | 7/2001 | Karin et al. | |
| 6,270,781 B1 | 8/2001 | Gehlsen | |
| 6,270,827 B1 | 8/2001 | Gaull et al. | |
| 6,296,832 B1 | 10/2001 | Ruoslahti et al. | |
| 6,296,868 B1 | 10/2001 | Valentine et al. | |
| 6,322,773 B1 | 11/2001 | Montgomery | |
| 6,329,155 B1 | 12/2001 | Nitsch et al. | |
| 6,350,438 B1 | 2/2002 | Witt et al. | |
| 6,355,297 B1 | 3/2002 | Sawatzki et al. | |
| 6,383,790 B1 | 5/2002 | Shokat | |
| 6,403,633 B2 | 6/2002 | Illig et al. | |
| 6,419,906 B1 | 7/2002 | Xu et al. | |
| 6,471,991 B2 | 10/2002 | Robinson et al. | |
| 6,503,483 B2 | 1/2003 | Shuch | |
| 6,555,543 B2 | 4/2003 | Bar-Or | |
| 6,569,839 B1 | 5/2003 | McKay | |
| 6,610,651 B1 | 8/2003 | Ruoslahti et al. | |
| 6,750,234 B2 | 6/2004 | Jaccobson et al. | |
| 6,780,844 B1 | 8/2004 | Reynolds | |
| 6,974,805 B2* | 12/2005 | Hu | 514/54 |
| 7,918,229 B2* | 4/2011 | Cumbie et al. | 128/898 |
| 7,982,008 B2 | 7/2011 | Bar-Or | |
| 2001/0025044 A1 | 9/2001 | Salituro et al. | |
| 2002/0001625 A1 | 1/2002 | Ballard et al. | |
| 2002/0081318 A1 | 6/2002 | Zaia et al. | |
| 2002/0115824 A1 | 8/2002 | Engler et al. | |
| 2002/0147144 A1 | 10/2002 | Sidelman | |
| 2002/0165220 A1* | 11/2002 | Heesch | 514/210.09 |
| 2003/0026794 A1* | 2/2003 | Fein | 424/94.2 |
| 2003/0130185 A1 | 7/2003 | Bar-Or | |
| 2003/0158111 A1 | 8/2003 | Bar-Or | |
| 2004/0014653 A1 | 1/2004 | Smith | |
| 2004/0234666 A1 | 11/2004 | Law et al. | |
| 2005/0089969 A1 | 4/2005 | Wissler et al. | |
| 2008/0214435 A1* | 9/2008 | Bonde | 514/2 |
| 2009/0008287 A1 | 1/2009 | Viggiano | |
| 2010/0022567 A1 | 1/2010 | Wurtman et al. | |
| 2011/0081717 A1* | 4/2011 | Inoue et al. | 435/320.1 |
| 2011/0237492 A1 | 9/2011 | Bar-Or | |

FOREIGN PATENT DOCUMENTS

| | | |
|---|---|---|
| EP | 752833 | 1/1997 |
| EP | 0760674 | 3/1997 |
| EP | 0862450 | 9/1998 |
| EP | 0804228 B1 | 6/2002 |
| GB | 1350197 | 4/1974 |
| JP | 03-056500 | 3/1991 |
| JP | 05-025032 | 2/1993 |
| JP | 10-203996 | 8/1998 |
| JP | 11-509840 | 8/1999 |
| JP | 2001-017122 | 1/2001 |
| JP | 2001-346588 | 12/2001 |
| KR | 1995-702421 | 7/1995 |
| WO | WO 82/03008 | 9/1982 |
| WO | WO 84/04453 | 11/1984 |
| WO | WO 92/18526 | 10/1992 |
| WO | WO 94/02148 | 2/1994 |
| WO | WO 95/24872 | 9/1995 |
| WO | WO 95/32707 | 12/1995 |
| WO | WO 96/06530 | 3/1996 |
| WO | WO 96/08232 | 3/1996 |
| WO | WO 97/01354 | 1/1997 |
| WO | WO 98/35551 | 8/1998 |
| WO | WO 99/02137 | 1/1999 |
| WO | WO 99/37236 | 7/1999 |
| WO | WO 00/06291 | 2/2000 |
| WO | WO 00/08946 | 2/2000 |
| WO | WO 00/66198 | 11/2000 |
| WO | WO 01/22837 | 4/2001 |
| WO | WO 01/25265 | 4/2001 |
| WO | WO 01/89463 | 11/2001 |
| WO | WO 01/90337 | 11/2001 |
| WO | WO 01/96547 | 12/2001 |
| WO | WO 02/04949 | 1/2002 |
| WO | WO 02/07695 | 1/2002 |
| WO | WO 02/11676 | 2/2002 |
| WO | WO 02/13775 | 2/2002 |
| WO | WO 02/064620 | 8/2002 |
| WO | WO 02/090530 | 11/2002 |
| WO | WO 03/031472 | 4/2003 |
| WO | WO 03/043518 | 5/2003 |

OTHER PUBLICATIONS

Songyang et al., "Use of an oriented peptide library to determine the optimal substrates of protein kinases," Current Biology, Nov. 1994, vol. 4(11), pp. 973-982.

Toomik et al., "A potent and highly selective peptide substrates for protein kinase C assay," Biochem J., Mar. 1997, vol. 322, part 2, pp. 455-460.

U.S. Appl. No. 09/678,202, filed Sep. 29, 2000, Bar-Or.

U.S. Appl. No. 60/413,694, filed Sep. 25, 2002, Bar-Or.

"Instructions: GelCode® Phosphoprotein Staining Kit," Pierce Chemical Co., Mar. 2001, pp. 1-3.

"P1253 Phosvitin from egg yolk," www.sigma-aldrich.com, 2007, updated, http://www.sigmaaldrich.com/catalog/search/ProductDetail/SIGMA/P1253?PrtPrv=1, p. 1.

Ahmed et al., "Phosvitin Phosphate Content: Implications for Prtein Kinase Assay," Biochim. Biophys. Acta., Jan. 23, 1975, vol. 377, pp. 80-83.

Aitken, "Protein Consensus Sequence Motifs," Mol. Biotechnol., 1999, vol. 12, pp. 241-253.

Aluko et al., "Characterization of oil-in-water emulsions stabilized by hen's egg yolk granule," Food Hydrocolloids, 1998, vol. 12, pp. 203-210.

Aluko et al., "Competitive Adsorption of Hen's Egg Yolk Granule Lipoproteins and Phosvitin in Oil-in-Water Emulsions," J. Agric. Food Chem., 1997, vol. 45, pp. 4564-4570.

Belperio et al., "CXC chemokines in angiogenesis," Journal of Leukocyte Biology, Jul. 2000, vol. 68, pp. 1-8.

Byrne et al., "Amino Acid sequence of phosvitin derived from the nucleotide sequence of part of the chicken vitellogenin gene," Biochemistry, 1984, vol. 23 pp. 4275-4279.

Byrne et al., Accession No. AAA98791, Gallus gallus vitellogenin, 1994, 1 page.

Calabokis et al., "Biochemical and enzymatic characterization of a partially purified casein kinase-1 like activity from *Trypanosoma cruzi*," Parasitol Int. 2002, vol. 51(1), pp. 25-39.

Casein Kinase I Peptide Substrate. Datasheet [online]. Promega Corporation, 2003 [retrieved on Nov. 19, 2003]. Retrieved from the Internet: <URL:http://www.promega.com/catalog/CatalogProducts.asp?catalog%5Fname=Promega%5FP . . . .

Casein Kinase I Peptide Substrate. Datasheet [online]. Promega Corporation, 2003 [retrieved on Nov. 25, 2003]. Retrieved from the Internet: <URL:http://www.promega.com/catalog/CatalogProducts.asp?catalog%5Fname=Promega%5FP . . . .

Casein Kinase II Peptide Substrate. Datasheet [online]. Promega Corporation, 2003 [retrieved on Nov. 25, 2003]. Retrieved from the Internet: <URL:http://www.promega.com/catalog/CatalogProducts.asp?catalog%5Fname=Promega%5FP . . . .

cdc2 Protein Kinase Peptide Substrate. Datasheet [online]. Promega Corporation, 2003 [retrieved on Nov. 25, 2003]. Retrieved from the Internet: <URL:http://www.promega.com/catalog/CatalogProducts.asp?catalog%5Fname=Promega%5FP . . . .

cGMP-Dependent Protein Kinase (PKG) Peptide Substrate. Datasheet [online]. Promega Corporation, 2003 [retrieved on Nov. 25, 2003]. Retrieved from the Internet: <URL:http://www.promega.com/catalog/CatalogProducts.asp?catalog%5Fname=Promega%5FP . . . .

Church et al., "Antithrombin action of phosvitin and other phosphate-containing polyanions is mediated by heparin cofactor II," FEBS Letters, 1988, vol. 237, pp. 26-30.

Cohen et al., "The development and therapeutic potential of protein kinase inhibitors," Current Opinion in Chemical Biology, 1999, vol. 3, pp. 459-465.

DNA—Dependent Protein Kinase Peptide Substrate. Datasheet [online]. Promega Corporation, 2003 [retrieved on Nov. 25, 2003]. Retrieved from the Internet: <URL:http://www.promega.com/catalog/CatalogProducts.asp?catalog%5Fname=Promega%5FP . . . .

Fujino et al., "Change in phosvitin kinase activity during early development of the sea urchin," Gamete Res, 1983, vol. 7, pp. 249-257.

Gill et al., "Assay of Cyclic Nucleotide-Dependent Protein Kinases," Advances in Cyclic Nucleotide Research, 1979, vol. 10, pp. 93-106.

Gln-Ala, see NCBI Sequence Viewer (2008, updated) http://www.ncbi.nlm.nih.gov/entrez/viewer.fcgi?db=protein&id=212879, p. 1.

Goulas et al., "Oligophosphopeptides of Varied Structural Complexity Derived from the Egg Phosphoprotein, Phosvitin," Journal of Protein Cehmistry, 1996, vol. 15(1), pp. 1-9.

Griffiths et al., "Modulation of leucocyte adhesion molecules, a T-cell chemotaxin (IL-8) and a regulatory cytokine (TNF-alpha) in allergic contact dermatitis (rhus dermatitis)," Br J. Dermatol, 1991, vol. 124(6), pp. 519-526.

Harvilicz, "Nutraceutical Toothpaste Debuts," Chemical Market Reporter, BNET business network, Jul. 1998, at http://findarticles.com/p/articles/mi_hb4250/is_/ai_n13189892, pp. 1-4, downloaded from internet on Dec. 17, 2008.

Hata et al., "Identification of a phosphopeptide in bovine αs 1-casein digest as factor influencing proliferation and immunoglobulin products in lymphocyte cultures," Journal of Sairy Research, 1998, vol. 65, pp. 569-578.

Ibanoglu et al., "Thermal denaturation and functional properties of egg proteins in the presence of hydrocolloid gums," Food Chem., 2007, vol. 101, pp. 626-633.

Jiang et al., "Phosphopeptides derived from hen egg yolk phosvitin: effect of molecular size on the calcuim-binding properties," Bioscience, Biotechnology, and Biochemistry, May 2001, vol. 65(5), pp. 1187-1190.

Jiang et al., "Preparation of novel functional oligophosphopeptides from hen egg yolk phosvitin," J. Agric Food Chem, 2000, vol. 48(4), pp. 990-994.

Jourd'Heuil et al., "Oxidant-regulation of gene expression in the chronically inflamed intestine," Keio J. Med., 1997, vol. 46(1), pp. 10-15 (Abstract Only).

Katayama et al., "Antioxidative stress activity of oligophosphopeptides derived from hen egg yolk phosvitin in Caco-2 cells," Journal of Agriculture and Food Chemistry, Feb. 8, 2006, vol. 54(3), pp. 773-778.

Kato et al., "Effects of Phosphate Residues on the Excellent Emulsifying Properties Phosphoglycoprotein Phosvitin," Agric. Biol. Chem., 1987, vol. 51(11), pp. 2989-2994.

Kemptide (PKA) Peptide Substrate. Datasheet [online]. Promega Corporation, 2003 [retrieved on Nov. 25, 2003]. Retrieved from the Internet: <URL:http://www.promega.com/catalog/CatalogProducts.asp?catalog%5Fname=Promega%5FP . . . .

Khan et al., "Effect of PRETEASE Digestion and Dephosphorylation on High Emulsifying Properties of Hen Egg Yolk Phosvitin," J. Agric. Food Chem., 1998, vol. 46, pp. 4977-4981.

Kipping et al., "Increased backbone flexibility in threonine45-phosphorylated hirudin upon pH change," Biochemistry, 2001, vol. 40, pp. 7957-7963.

Kreegipuu et al., "PhosphoBase, a database of phosphorylation sites: release 2.0." Nucleic Acids Research, 1999, vol. 27(1), pp. 237-239.

Le Denmat et al., "Characterization of emulsion properties and of interface composition in O/W emulsions prepared with hen egg yolk, plasma and granules," Food Hycolloids, 2000, vol. 14, pp. 539-549.

Lee et al., "Antioxidant Activity of Phosvitin in Phosphatidylcholine Liposomes and Meat Model Systems," J. of Food Science, 2002 vol 67(1) (Abstract Only).

Lee et al., "Inhibition of p38 MAP kinase as a therapeutic strategy," Immunopharmacology, 2000, vol. 47(2), pp. 185-201 (Abstract Only).

Losso et al., "A Simple Procedure for the Isolation of Phosvitin from Chicken Egg Yolks," Egg Uses and Processing Technologies: New Developments (Sim and Nakai, eds.), Cab International, Oxon, UK, 1994, pp. 150-157.

Miller et al., Dephosphorylation of chicken riboflavin-binding protein and phosvitin decreases their uptake by oocytes, Journal of Biological Chemistry 1982, 257(12):6818-6824.

Mukaida et al., "Regulation of human interleukin 8 gene expression and binding of several other members of the intercrine family to receptors for interleukin-8," Adv. Exp. Med. Biol, 1991, vol. 305, pp. 31-38.

Nakamura et al., "Antioxidant Activity of a Maillard-Type Phosvitin-Galactomannan Conjugate with Emulsifying Properties and Heat Stability," J. Agric. Food Chem., 1998, vol. 46, pp. 3958-3963.

Neurogranin(28-43) (PKC) Peptide Substrate. Datasheet [online]. Promega Corporation, 2003 [retrieved on Nov. 25, 2003]. Retrieved from the Internet: <URL:http://www.promega.com/catalog/CatalogProducts.asp?catalog%5Fname=Promega%5FP . . . .

Okamoto et al., "The Interleukin-8 AP-1 and KB-like Sites Are Genetic End Targets of FKBO6-sensitive Pathway Accompanied by Calcium Mobilization," The Journal of Biological Chemistry, Mar. 1994, vol. 269(11), pp. 8582-8589.

PDR Medical Dictionary, 1st ed., 1995, p. 799.

PhosphoBase v. 2.0: A Database of Phosphorylation Sites, 2003, 1 page, http://www.cbs.dtu.dk/databases/PhosphoBase/ (Original website http://www.cbs.dtu.dk/databases/PhosphoBase/).

PhosphoBase v2.0. A database of phosphorylation sites, provided by Center for Biological Sequence Analysis (CBS) [online] [retrieved on Nov. 26, 2002]. Retrieved from the Internet:<URL:http://www.cbs.dtu.dk/databases/PhosphoBase/.

Phosphoprotein Database (PPDB), Introduction to the phosphoprotein databases* [online] [retrieved on Nov. 26, 2002]. Retrieved from the Internet:<URL:http://www-lmmb.nciferf.gov/phosphoDB/ .

Platt et al., "Protein phosphorylation in *Mycoplasma gallisepticum*," Eur. J. Biochem., 1988, vol. 176(1), pp. 61-67.

Queiroz-Claret et al., "Modifications of phosvitin by an immobilized protein phosphatase from *Yarrowia lipolytica*," Nahrung, 1998, vol. 42(3-4), pp. 166-167.

Reimerdes et al., "Determination of Proteolytic Activities on Casein Substrates," Methods in Enzymology, 1976, vol. 45, pp. 26-28.

Shanley, "Phosphates: counterregulatory role in inflammatory cell signaling," Crit Care Med, 2002, vol. 30(1)(Suppl.), pp. S80-S88.

Songyang et al., "Use of an oriented peptide library to determine the optimal substrates of protein kinases," Curr Biol, 1994, vol. 4(11), pp. 973-982 (Abstract Only).

Stewart et al., "Nucleotide sequences of bovine alpha S1-and kappa-casein cDNAs," Nucleic Acid Res, 1984, vol. 12(9), pp. 3895-3907.

Strieter et al., "Role of C-X-C chemokines as regulators of angiogenesis in lung cancer," Journal of Leukocyte Biology, May 1995, vol. 57, pp. 752-762.

Sundararajan et al., "Preparation and amino acid composition of enzymically dephosphorylated casesin," Biochem. J., Feb. 1957, vol. 65(2), pp. 261-266.

Takeishi et al., "In Vivo Phosphorylation of Cardiac Troponin I by Protein Kinase Cβ2 Decreases Cardiomyocyte Calcium Responsiveness and Contractility in Transgenic Mouse Hearts," J. Clin. Invest., Jul. 1998, vol. 102(1), pp. 72-78.

Van Hekken et al., "Functional properties of dephosphorylated bovine whole casein," J. Dairy Science, Jun. 1993, vol. 76(11), pp. 3384-3391.

Wikipedia, (2009, updated), "Nutraceutical," en.wikipedia.org/wiki/Nutraceutical, pp. 1-2.

Worthington Casein, Alpha, Manual Page, Worthington-biochem.com [online] [retrieved on Nov. 20, 2003]. Retrieved from the Internet:<URL:http://www.worthington-biochem.com/CASA/default.html.

Wu et al., "Identifying substrate motifs of protein kinases by a random library approach," Biochemistry, 1994, vol. 33(49), pp. 14825-14833 (Abstract Only).

Xu et al., "Antioxidant activity of tyrptic digests of hen egg yolk phosvitin," J. Sci. Food Agric., 2007, vol. 87(14) pp. 2604-2608 (Abstract Only).

Zhai et al., "Recombinant rabbit muscle casein kinase I alpha is inhibited by heparin and activated by polylysine," Biochem Biophys Res Commun., 1992, vol. 189(2), pp. 944-949.

International Search Report for International (PCT) Application No. PCT/US03/37901, mailed May 30, 2006.

International Preliminary Examination Report for International (PCT) Application No. PCT/US03/37901, mailed May 30, 2006.

Supplementary European Search Report for European Patent Application No. 03799853.1, dated Oct. 26, 2009.

"Composition of Cow's milk" reference at www.food-allergens.de/password-2002/symposium-4-1/cows-milk/cows-milk-composition.html, 2002, pp. 1-2.

Sarno et al. "Selectivity of 4,5,6,7-tetrabromobenzotriazole, an ATP site-directed inhibitor of protein kinase CK2 ('casein kinase-2')." FEBS Letters, May 2001, vol. 496 No. 1, pp. 44-48.

Walter et al. "Induced Release of Cell Surface Protein Kinase Yields CK1-and CK2-like Enzymes in Tandem." The Journal of Biological Chemistry, Jan. 1996, vol. 271, No. 1, pp. 111-119.

Smith et al., "Inhibition of interleukin 8 attenuates angiogenesis in bronchogenic carcinoma," The Journal of Experimental Medicine, 1994, vol. 179, No. 5, pp. 1409-1415.

* cited by examiner

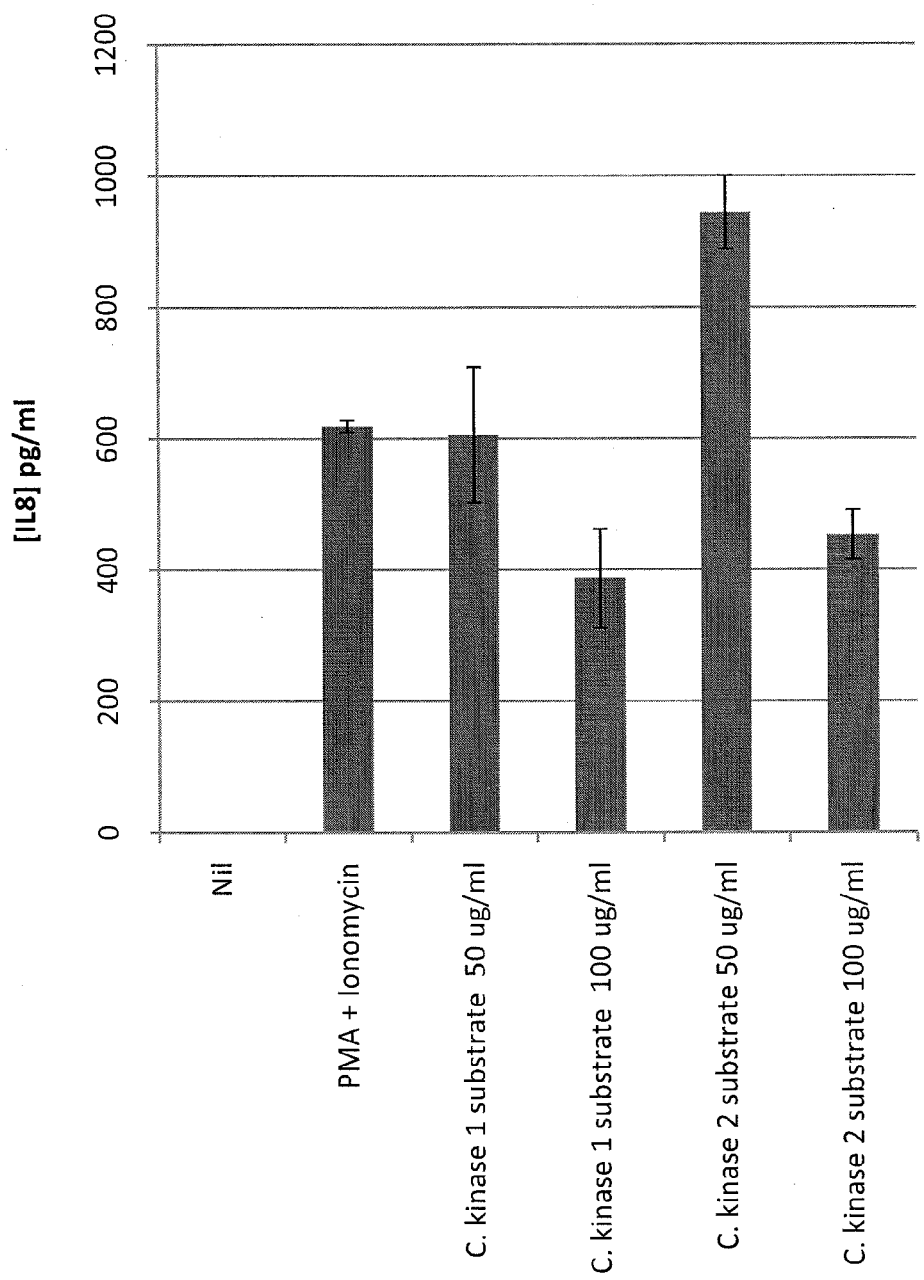

TREATMENT OF DISEASES AND CONDITIONS MEDIATED BY INCREASED PHOSPHORYLATION

CROSS REFERENCE TO RELATED APPLICATIONS

The present application is a divisional of U.S. patent application Ser. No. 10/723,247, filed Nov. 25, 2003, which claims the benefit of U.S. Provisional Patent Application Ser. No. 60/429,924, filed Nov. 27, 2002; each of the above-identified applications are incorporated fully herein by reference.

FIELD OF THE INVENTION

The invention relates to methods for the treatment of diseases and conditions mediated by increased phosphorylation, such as inflammation and cancer. The invention also relates to methods for the inhibition of increased phosphorylation in cells, tissues and organs. The methods utilize a phosphate acceptor compound (PAC). The invention also relates to products comprising a PAC.

BACKGROUND OF THE INVENTION

Signal transduction is the cascade of processes by which an extracellular signal interacts with a receptor at the cell surface to ultimately effect a change in cell functioning. Protein phosphorylation plays a key role in signal transduction. Protein phosphorylation is performed by protein kinases, and virtually all aspects of cell functioning in one way or another depend on kinase activity. Not surprisingly, then, abnormal (usually increased) kinase activity has been related to a host of diseases and disorders.

Protein kinases catalyze the transfer of phosphate from adenosine triphosphate (ATP) to specific amino acid residues (almost always a serine, threonine or tyrosine residue) of proteins. Several features of kinases make them ideally suited to function in signal transduction. One is that they often have overlapping target substrate specificities which allows "cross-talk" among different signaling pathways, allowing for the integration of different signals. A second feature is that the kinases are organized into several modular functional domains. These domains appear to have been mixed and matched through evolution to produce the large protein kinase family, and the kinases are structurally and catalytically similar. A third feature is their speed. The kinetics of phosphorylation and dephosphorylation are extremely rapid, providing for rapid responses and short recovery times, which in turn makes repeated signal transmission possible.

Given their roles in numerous diseases and in signal transduction, considerable effort has been made to develop protein kinase inhibitors. As far as is known, all of this effort has been directed at developing specific inhibitors that inhibit only a single kinase. However, the effort to find specific inhibitors of single kinases is a daunting task. Recent estimates predict the presence of greater than 2,000 protein kinase genes in the human genome. Shanley, *Crit. Care Med.*, 30 (No. 1, Suppl): S80-S88 (2002); Cohen, *Current Opinion in Chemical Biology*, 3:459-465 (1999). Also, the very features described above which make kinases so useful in signal transduction, and which have made them evolve to become central to almost every cellular function, also make them extremely difficult to study and understand. U.S. Pat. No. 6,383,790. Unfortunately, the enormous number of kinases and the similarities between them have frustrated the discovery and design of specific inhibitors. U.S. Pat. No. 6,383,790. Further, because the kinase networks are highly degenerate and interconnected in unknown ways, there is considerable uncertainty with regard to which kinases should be targeted for inhibition to treat many diseases. U.S. Pat. No. 6,383,790. Moreover, it is by no means clear that a specific inhibitor of a given kinase will have any effect on a given disease. U.S. Pat. No. 6,383,790. Since kinases can be highly promiscuous, there is a significant chance that inhibiting one kinase will simply force another kinase to take its place. U.S. Pat. No. 6,383,790.

From the foregoing it is clear that it would be desirable to have methods and products for reducing unwanted phosphorylation without the need to identify specific inhibitors for individual kinases. It would further be desirable to have methods and products for the effective treatment of diseases and conditions mediated by increased phosphorylation without the need to identify specific inhibitors for individual kinases. The invention provides such methods and products.

SUMMARY OF THE INVENTION

In particular, the invention provides methods and products for the treatment of diseases and conditions mediated by increased phosphorylation. The invention also provides methods and products for inhibiting increased phosphorylation in cells, tissues and organs. The methods and products of the invention utilize a phosphate acceptor compound (PAC). A PAC is a compound that is capable of being phosphorylated. Phosphorylation of PACs has the effect of reducing the amount of ATP and phosphate groups available for phosphorylation by kinases of their normal substrates, thereby inhibiting the unwanted increased phosphorylation. Thus, the identity of the PACs is not crucial, and it is not necessary to know which specific kinases are involved in causing the unwanted increased phosphorylation.

BRIEF DESCRIPTION OF THE DRAWING

FIG. 1: A bar graph showing the amount interleukin 8 (IL-8) versus treatment.

DETAILED DESCRIPTION OF THE PRESENTLY-PREFERRED EMBODIMENTS OF THE INVENTION

As described above, the invention provides methods and products for the treatment of diseases and conditions mediated by increased phosphorylation. The invention also provides methods and products for inhibiting increased phosphorylation in cells, tissues and organs. The methods and products utilize a phosphate acceptor compound (PAC).

"Treat" and variations thereof are used herein to mean to cure, prevent, eliminate, ameliorate, alleviate or reduce the severity of a disease or condition, or of at least some of the symptoms or effects thereof.

As used herein a "disease or condition mediated by increased phosphorylation" means a disease or condition caused by, exacerbated by or involving increased phosphorylation of proteins and/or peptides of the animal suffering from the disease or condition.

"Increased phosphorylation" means a level of phosphorylation above the normal level found in the absence of such a disease or condition. Increased phosphorylation is caused by a net increase in kinase activity which, in turn, is caused by increased kinase activity, decreased phosphatase activity, or both.

"Inhibit" and variations thereof are used herein to mean reduce, eliminate or prevent.

A. Phosphate Acceptor Compounds

As used herein, a "phosphate-acceptor compound" or "PAC" is a compound that is capable of being phosphorylated. PACs may be extracellular PACs ("EPACs") or intracellular PACs ("IPACs").

Phosphorylation of PACs has the effect of reducing the amount of ATP and phosphate groups available for phosphorylation by kinases of their normal substrates, thereby inhibiting unwanted increased phosphorylation. Thus, the identity of the PACs is not crucial, and it is not necessary to know which kinase(s) are involved in causing the unwanted increased phosphorylation.

In cases where it is known or suspected that a particular kinase is responsible for, or at least involved in causing, the unwanted increased phosphorylation, one or more substrates of the kinase, if known, can be used as the PAC(s). The use of such substrates may more efficiently or completely inhibit the unwanted increased phosphorylation, but the use of such substrates is not necessary. Further, the use of such substrates may not result in any improvement in inhibition since, as noted above, kinases can be highly promiscuous, and other kinases may simply assist the kinase suspected of being responsible for, or involved in causing, the unwanted increased phosphorylation in performing its function.

1. Extracellular Phosphate Acceptor Compounds

By "extracellular" is meant that the extracellular phosphate acceptor compound (EPAC) does not penetrate sufficiently inside cells to interact with intracellular pathways involving phosphorylation. Doing so could seriously damage or even kill the cells. The EPAC may remain entirely outside the cell, may interact with or bind to receptors and/or other molecules found on or in cell membranes, or may even penetrate the cellular membrane, as long as the EPAC does not penetrate it in such a manner that it can interact with intracellular pathways involving phosphorylation.

The EPACs are substrates for phosphorylation by membrane-bound and/or circulating/soluble kinases. EPACs compete with the normal substrates to be phosphorylated by kinases, and phosphorylation of the EPACs reduces or prevents phosphorylation of extracellular and intracellular proteins, peptides and other compounds (phosphorylation of the EPACs has the effect of reducing the amount of ATP and phosphate groups available for phosphorylation of both extracellular and intracellular proteins, peptides and other compounds). Also, phosphorylation of the EPACs by membrane-bound kinases reduces or prevents signal transduction from the outside to the inside of cells.

In addition, phosphorylated proteins and peptides can bind metal ions, including iron and copper ions. As a result, they can function as antioxidants. Thus, the EPAC proteins and peptides of the invention should provide an added antioxidant benefit after they are phosphorylated.

Suitable EPACs include proteins and peptides that comprise one or more phosphorylation sites. As noted above, virtually all protein kinases phosphorylate serine, threonine and/or tyrosine residues, and over 1000 phosphorylation sites comprising serine, threonine and/or tyrosine residues are now known. See, e.g., Kreegipuu et al., "PhosphoBase, a database of phosphorylation sites: release 2.0," *Nucleic Acids Res.*, 27(1):237-239 (1999) and www.cbs.dtu.dk/databases/PhosphoBase/. The proteins and peptides may be naturally-occurring proteins and peptides, fragments of such proteins and peptides and synthetic proteins and peptides (including mutated and partially synthetic forms of naturally-occurring proteins and peptides and wholly synthetic proteins and peptides) that comprise at least one phosphorylatable amino acid. The proteins and peptides must be of a sufficient size (typically greater than about 20 amino acids in length) and/or have a charge (i.e., be hydrophilic) that causes them to remain extracellular.

At least one of the phosphorylation sites of an EPAC must, of course, be unphosphorylated for it to function as a phosphate acceptor. Unphosphorylated proteins and peptides can be produced by chemical synthesis using methods well known in the art. For instance, the proteins and peptides can be synthesized by standard solid-phase peptide synthesis methods. Suitable techniques are well known in the art, and include those described in Merrifield, in *Chem. Polypeptides*, pp. 335-61 (Katsoyannis and Panayotis eds. 1973); Merrifield, *J. Am. Chem. Soc.*, 85, 2149 (1963); Davis et al., *Biochem. Int'l*, 10, 394-414 (1985); Stewart and Young, *Solid Phase Peptide Synthesis* (1969); U.S. Pat. Nos. 3,941,763 and 5,786,335; Finn et al., in *The Proteins*, 3rd ed., vol. 2, pp. 105-253 (1976); and Erickson et al. in *The Proteins*, 3rd ed., vol. 2, pp. 257-527 (1976). Proteins and peptides made by chemical synthesis may be comprised of L-amino acids, D-amino acids, or combinations thereof, except that the phosphorylatable amino acids (serines, threonines and/or tyrosines) are preferably not D-amino acids. The use of proteins and peptides composed of one or more D-amino acids is desirable because proteins and peptides containing D-amino acids are resistant to proteolytic enzymes, such as those that would be encountered upon administration of the proteins and peptides to an animal or that would be present in an excised organ perfused with a solution containing the proteins or peptides. Also, the use of D-amino acids should not alter the ability of the proteins or peptides to be phosphorylated.

Unphosphorylated proteins and peptides can also be produced in bacteria by recombinant DNA techniques. See U.S. Pat. No. 5,942,254. Phosphorylated proteins and peptides can be produced in other hosts and then dephosphorylated as described below, Recombinant DNA techniques, vectors and reagents for expressing proteins in bacteria and other hosts are well known in the art. See, e.g., Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989).

Some naturally-occurring unphosphorylated proteins and peptides that can function as EPACs are known. For instance, $\alpha_{S1}$-casein found in human colostrum is substantially unphosphorylated.

Proteins and peptides which are phosphorylated must be at least partially dephosphorylated prior to use. As used herein "at least partially dephosphorylated" means that the number of phosphorylated amino acids present in the population of proteins or peptides is reduced by at least about 10%. The number of phosphorylated amino acids present in the population of proteins or peptides is preferably reduced by at least about 35%, more preferably by at least about 50%, even more preferably by at least about 70%, most preferably by at least about 90%, prior to use. Also, as used herein, those proteins and peptides produced or found unphosphorylated or substantially unphosphorylated come within the definition of proteins and peptides that are "at least partially dephosphylated."

Methods of dephosphorylating proteins and peptides that are phosphorylated are well known. In particular, proteins and peptides can be dephosphorylated enzymatically or chemically. See, e.g., U.S. Pat. Nos. 6,355,297 and 5,068,118, Miller et al., *J. Biol. Chem.*, 257:6818-6824 (1982), Jiang and Mine, *J. Agric. Food Chem.*, 48:990-994 (2000), and Example 2. For enzymatic dephosphorylation, any of a large number of phosphatases can be employed. Preferred is an acid phosphatase or an alkaline phosphatase. These phosphatases are non-specific phosphomonoesterases and can be used to dephosphorylate most proteins and peptides. Preferred is an alkaline phosphatase, most preferably from *Escherichia coli*. Also, serine/threonine phosphatases, tyrosine phosphatases, tyrosine/threonine phosphatases and combinations of the foregoing could be used. Suitable phosphatases are available commercially from numerous companies, including Sigma-Aldrich Co., Worthington Biochemical Corp., Takara Bio Inc., CHIMERx, and Promega. In chemical dephosphorylation, the phosphates are cleaved off by heating the proteins and peptides (preferably at 35° C.-70° C.) at alkaline pH (preferably about pH 10-12) for a time sufficient to obtain the desired amount of dephosphorylation. The presently preferred conditions are given in Example 2 and Jiang and Mine, *J. Agric. Food Chem.*, 48:990-994 (2000).

The extent of phosphorylation of the protein or peptide before and after dephosphorylation can be determined. Suitable methods are well known in the art. See, e.g., Miller et al., *J. Biol. Chem.*, 257:6818-6824 (1982) and Example 2. Also, kits are available commercially that can be used to measure phosphorylation levels. Such kits are available from, e.g., Pierce (Phosphoprotein Phosphate Estimation Kit based on the alkaline hydrolysis of phosphate from serine and threonine residues followed by quantification of the phosphate by the use of Malachite Green and ammonium molybdate). In addition, an immunoassay using appropriate antibodies (e.g., antibodies specific for phosphorylated serine, threonine and tyrosine residues) could be used. Such antibodies are available commercially from, e.g., Zymed Laboratories.

Specific proteins useful in the practice of the invention include phosvitins and fragments thereof. Phosvitins are egg yolk proteins. Chicken phosvitin has been reported to have 109 phosphorylation sites (Miller et al., *J. Biol. Chem.*, 257:6818-6824 (1982)), and is particularly preferred for use herein. Chicken phosvitin can be prepared by methods well known in the art (see, e.g., Japanese application JP 3056500) and is available commercially from, e.g., U.S. Biochemical Amersham and Sigma-Aldrich. It can be dephosphorylated as described above.

Other suitable proteins for use in the practice of the invention include caseins. Whole casein, α-casein, one of the several isoforms of α-casein, β-casein, γ-casein and/or κ-casein and/or fragments of any of the foregoing can be used. Caseins have multiple phosphorylation sites. For instance, β-casein has five phosphorylation sites. Whole caseins, α-caseins, isoforms of α casein, β-caseins, γ-caseins, and κ-caseins are available commercially (from, e.g., Sigma-Aldrich) or can made be prepared by methods well known in the art (see, e.g., U.S. Pat. Nos. 5,068,118, 5,739,407, 5,795,611, 5,942,274 and 6,232,094 and http://wvvw.worthington-biochem.com/CASA). Preferred are caseins made by recombinant DNA techniques in bacteria, since they will not be phosphorylated. Also, as noted above, $\alpha_{S1}$ casein from human colostrum is naturally unphosphorylated and is, therefore, very convenient to use. It is available commercially from Sigma-Aldrich. Dephosphorylation of caseins, if necessary, can be performed as described above, See, e.g, U.S. Pat. Nos. 6,355,297 and 5,068,118.

Other suitable EPACs for use in the practice of the invention include blood proteins and peptides. If the proteins and/or peptides administered to an animal are from the same species of animal as the one being treated, the proteins and/or peptides should not be immunogenic. Thus, homologous blood proteins and peptides are particularly suitable for systemic administration.

One or a mixture of blood proteins and/or peptides can be used as EPACs. For instance, all of the proteins and peptides in a pooled plasma or pooled serum sample could be dephosphorylated and used in the practice of the invention. Alternatively, individual plasma proteins or peptides having one or more phosphorylation sites could be isolated from plasma or serum or could be produced by recombinant DNA techniques and used in the practice of the invention.

It has been found that human albumin can be phosphorylated. However, acetylation of the albumin was necessary for phosphorylation to take place. It is believed that it is the serine at position 202 that is phosphorylated and the lysine at position 199 that is acetylated. It is also believed that, in albumin which is not acetylated, the positively charged side chain of the lysine interacts with the negatively charged serine, blocking phosphorylation of the serine. When the lysine is acetylated, its charge is neutralized and it no longer interacts with the serine, and the serine can be phosphorylated. Acetylated human albumin has also been found to be present in plasma and serum, especially in individuals who are taking aspirin, and it could be isolated from pooled plasma or serum, dephosphorylated, and used in the practice of the present invention. Alternatively, albumin could be produced by recombinant DNA techniques (preferably in bacteria so it will not be phosphorylated) and acetylated. Methods of acetylating proteins are well known. For instance, albumin can be acetylated by incubating plasma (containing esterases) with 1 mM aspirin for 1 hour at 37° C., and the acetylated albumin isolated from the plasma by methods well known in the art. Also, serum or albumin (preferably albumin produced by recombinant DNA techniques) can be incubated with aspirin in the presence of an esterase or with N-acetyl aspartate in the presence of an acylase to acetylate the albumin. Albumin could also be acetylated using acetic anhydride. Of course, other acylations, such as methylation, could be performed instead of acetylation.

Also, a peptide comprising the albumin sequence from position 199 to position 202 can be prepared and acetylated. The sequence from position 199 to position 202 of albumin is Lys Cys Ala Ser [SEQ ID NO:1]. Other amino acids could be substituted for the cysteine and alanine residues between the lysine and serine residues, and the serine residue could be replaced by a threonine or tyrosine residue. Also, additional amino acids could be added to either end. Also the number of amino acids between the serine and lysine residues can be varied from 1-3, and the sequence repeated one or more times. Thus, another peptide useful in the practice of the invention is Lys Ala Ser Ser Ala Lys [SEQ ID NO:2], wherein both lysine residues are acetylated. In the case of EPACs, the amino acids substituted for the cysteine and/or alanine and/or added to either end should include sufficient charged amino acids so that the peptides will be hydrophilic and/or add enough amino acids so that the peptides will be at least 20 amino acids long. In particular, such peptides preferably will have the following sequences:

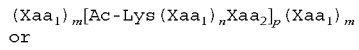

or

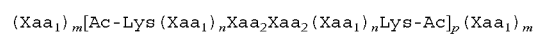

wherein:
Ac is an acyl group;
Xaa$_1$ is any amino acid;
Xaa$_2$ is serine, threonine or tyrosine;
m is 0-10;
n is 1-3;
p is 1-5; and
m, n and p are selected so that the total number of amino acids is at least about twenty and/or each Xaa$_1$ is selected so that the peptide will be hydrophilic.

Additional suitable EPACs for use in the practice of the invention include known kinase substrates. Many such kinase substrates are known, and some are available commercially from, e.g., Sigma-Aldrich and Promega. As noted above, the PACs act nonspecifically to reduce the amount of available ATP and phosphate groups, and these substrates may be used as EPACs regardless of the identity of the kinase(s) responsible for, or involved in causing, the unwanted increased phosphorylation.

Other suitable EPACs for use in the practice of the invention include synthetic proteins and peptides comprising at least one phosphorylatable amino acid. For instance, a protein or peptide comprising one or more serine, threonine and/or tyrosine residues can be used. Serine is the most-commonly phosphorylated amino acid, so the protein or peptide could comprise only serines. Preferably, however, the protein or peptide contains all three of these amino acids. Also preferably, the serine, threonine and/or tyrosine residues are spaced apart by one or more other amino acids. As noted above, if a lysine is within 1-3 amino acids of a serine, the lysine should preferably be acylated. Since the proteins and peptides are EPACs, they should contain at least about 20 amino acids and/or be charged (i.e., be hydrophilic). Thus, preferably, some of the other amino acids besides the serines, threonines and/or tyrosines are charged amino acids. One protein or peptide with one or more phosphorylatable amino acids, preferably a multiplicity of such amino acids, could be used. Alternatively, a cocktail of peptides, each comprising a single phosphorylatable amino acid, could be used. As used herein, "synthetic" means not naturally occurring.

Since kinases are highly promiscuous, it is anticipated that even random sequences comprising one or more serine, threonine and/or tyrosine residues will be phosphorylated. However, in a preferred embodiment, the synthetic protein or peptide will comprise one or more known phosphorylation sites. As noted above, over 1000 phosphorylation sites comprising serine, threonine and/or tyrosine residues are now known. See, e.g., Kreegipuu et al., "PhosphoBase, a database of phosphorylation sites: release 2.0," *Nucleic Acids Res.,* 27(1):237-239 (1999) and www.cbs.dtu.dk/databases/PhosphoBase/. See also, Aitken, *Mol. Biotechnol.,* 12:241-53 (1999). Also, methods have been developed for identifying phosphorylatable peptides from random peptide libraries. See Wu et al., *Biochemistry,* 13:14825-14833 (1994) and Songyang et al., *Curr. Biol.,* 4:973-982 (1994). Since the EPACs act nonspecifically, the identity of the phosphorylation sites is not critical. When a plurality of phosphorylation sites is used, each phosphorylation site may be the same or different than the other phosphorylation site(s).

2. Intracellular Phosphate Acceptor Compounds

By "intracellular" is meant that the intracellular phosphate acceptor compounds (IPACs) penetrate sufficiently inside cells to interact with intracellular pathways involving phosphorylation. Preferably, the IPACs will pass through the cellular membrane into the cytoplasm of the cell.

The IPACs are substrates for phosphorylation and, once inside the cells, the IPACs will compete with the normal substrates to be phosphorylated by intracellular kinases. Phosphorylation of the IPACs inhibits phosphorylation of intracellular proteins, peptides and other compounds and will inhibit signal transduction processes inside cells. Given the critical nature of phosphorylation for cell functioning, it is expected that IPACs will seriously harm or kill the cells that they enter. Thus, they should only be used to treat diseases and conditions, such as cancer, where the death of cells is desired or can be tolerated. Preferably, the IPACs will be targeted as described below so that they will enter only the cells whose death is desired. Targeting is particularly important when they are administered systemically.

Suitable IPACs include peptides that comprise one or more phosphorylation sites. The peptides may be naturally-occurring peptides, fragments of naturally-occurring proteins and synthetic peptides (including mutated or partially synthetic forms of naturally-occurring peptides and protein fragments and wholly synthetic peptides that comprise at least one phosphorylatable amino acid). The peptides should preferably be less than about 20 amino acids in length, more preferably less than about 10 amino acids in length, most preferably less than about 5 amino acids in length, since shorter peptides are better able to enter cells. To enhance the ability of the peptides and fragments to penetrate cell membranes, the peptides will preferably be hydrophobic and/or comprise an arginine oligomer (see Rouhi, *Chem. & Eng. News,* 49-50 (Jan. 15, 2001)). The arginine oligomer will preferably contain 6-9 Arg residues (see Rouhi, *Chem. & Eng. News,* 49-50 (Jan. 15, 2001). The use of an arginine oligomer may be particularly desirable when the peptide is to be administered topically or transdermally. The peptides may be synthesized and, if necessary, dephosphorylated as described above.

Specific suitable IPACs include peptides of the sequences:

(Xaa$_1$)$_m$[Ac-Lys(Xaa$_1$)$_n$Xaa$_2$]$_p$(Xaa$_1$)$_m$ or (Xaa$_1$)$_m$[Ac-Lys(Xaa$_1$)$_n$Xaa$_2$Xaa$_2$(Xaa$_1$)$_n$Lys-Ac]$_p$(Xaa$_1$)$_m$ wherein:
Ac is an acyl group;
Xaa$_1$ is any amino acid;
Xaa$_2$ is serine, threonine or tyrosine;
m is 0-10;
n is 1-3;
p is 1-5; and
m, n and p are selected so that the total number of amino acids is less than about twenty and each Xaa$_1$ is selected so that the peptide will be hydrophobic.

Additional suitable IPACs for use in the practice of the invention include known kinase substrates able to penetrate cells. Preferred are those which are hydrophobic and comprise less than about 20 amino acids.

Other suitable IPACs for use in the practice of the invention include synthetic peptides comprising at least one phosphorylatable amino acid. For instance, a peptide comprising one or more serine, threonine and/or tyrosine residues can be used. Serine is the most-commonly phosphorylated amino acid, so the peptide could comprise only serines. Preferably, however, the protein or peptide contains all three of these amino acids. Also preferably, the serine, threonine and/or tyrosine residues are spaced apart by one or more other amino acids. Since the peptides are IPACs, they should preferably contain less than about 20 amino acids and be hydrophobic. Thus, some of the other amino acids besides the serines, threonines and/or tyrosines should be uncharged amino acids. One peptide with one or more phosphorylatable amino acids, preferably a multiplicity of such amino acids, could be used. Alternatively, a cocktail of peptides, each comprising a single phosphorylatable amino acid, could be used.

Since kinases are highly promiscuous, it is anticipated that even random sequences comprising one or more serine, threonine and/or tyrosine residues will be phosphorylated. However, in a preferred embodiment, the synthetic peptide will comprise one or more known phosphorylation sites. As noted above, over 1000 phosphorylation sites comprising serine, threonine and/or tyrosine residues are now known. See, e.g., Kreegipuu et al., "PhosphoBase, a database of phosphorylation sites: release 2.0," *Nucleic Acids Res.*, 27(1):237-239 (1999) and www.cbs.dtu.dk/databases/PhosphoBase/. See also, Aitken, *Mol. Biotechnol.*, 12:241-53 (1999). Also, methods have been developed for identifying phosphorylatable peptides from random peptide libraries. See Wu et al., *Biochemistry*, 13:14825-14833 (1994) and Songyang et al., *Curr. Biol.*, 4:973-982 (1994). Since the IPACs act nonspecifically, the identity of the phosphorylation sites is not critical. When a plurality of phosphorylation sites is used, each phosphorylation site may be the same or different than the other phosphorylation site(s).

3. Targeting of Phosphate Acceptor Compounds

For administration to animals, the PACs can be targeted to a selected cell, tissue or organ. Targeting of the PACs will concentrate their effectiveness on the targeted cells, tissues or organs, reduce the likelihood of deleterious side effects, and decrease the dose that will need to be given. In the case of IPACs, targeting is highly desirable when they are administered systemically, and targeting will reduce or prevent unnecessary cell damage and death when other modes of administration are employed.

As used herein, "selected" cells, tissues and organs are those intended to be affected by the PAC. In the case of IPACs, the "selected" cells, tissues and organs are those intended to be impaired, damaged or destroyed by the IPAC. Selected cells, tissues and organs are also sometimes referred to herein as target cells, tissues and organs.

Numerous methods of targeting therapeutic compounds to selected cells or to a selected tissue or organ are known in the art and can be used to target the PACs of the invention to cells, tissues or organs. For instance, a PAC can be conjugated to a targeting molecule. The targeting molecule can be a specific ligand known to be reactive with a target cell, tissue or organ; such as receptor-specific ligands (e.g., a chemokine or growth factor) or antibodies specific for an antigen on the surface of the cell, tissue or organ. Suitable antibodies include polyclonal antibodies, omniclonal antibodies, monoclonal antibodies, bispecific antibodies, humanized antibodies, chimeric antibodies, single-chain antibodies, Fab fragments, F(ab')$_2$ fragments, fragments produced by an Fab expression library, epitope-binding fragments of any of the foregoing, and complementarity determining regions (CDRs). The targeting molecule can also be one of the homing molecules described below.

Another possibility is the use of multivalent antibodies. See, e.g., U.S. Pat. No. 5,861,156, the complete disclosure of which is incorporated herein by reference. For instance, a multivalent antibody that binds to a PAC and to a binding protein reactive with a cell surface marker of the target cell, tissue or organ could be used. After all three have been administered to an animal, the PAC will be bound to the multivalent antibody which, in turn, will be bound to the binding protein which, in turn, will be bound to the cell surface marker on the target cell. Preferably, the binding protein is a monospecific binding protein, such as Fab and F(ab)'$_2$ fragments, Fab fusion proteins, single-chain Fv proteins (single-chain antibodies), single-chain Fv fusion proteins, chimeric antibody proteins (e.g., recombinant antibody proteins derived from transfectoma cells), chimeric single-chain proteins and other single-chain fusion Fv analog proteins, such as single-chain T-cell receptors. U.S. Pat. No. 5,861,156 reports that such monospecific binding proteins have a unique ability to penetrate solid tumors and to be rapidly cleared from the circulation if not localized at a target site, making them extremely suitable for treatment of tumors. The multivalent antibody is any multivalent antibody, including polyclonal antibodies, monoclonal antibodies, heterobispecific antibodies, fragments of any of the foregoing, chimeric antibodies, bispecific single-chain antibodies, homodimeric IgG molecules, etc. In another embodiment, a cocktail of binding proteins is used, each binding protein being specific for a different surface marker on a target cell and each labelled with a moiety (e.g., a peptide tag) recognized by the multivalent antibody to allow multi-site targeting of a target cell. The multivalent antibody also recognizes the PAC, as well as the moiety. Thus, since each type of target cell has its own unique cell surface marker profile, the PAC can be targeted to the target cell with greater specificity and selectivity than with the use of a single binding protein specific for a single cell surface marker.

Proteins, peptides and other molecules that home to particular cells, tissues or organs can be identified by an in vivo panning technique. See U.S. Pat. Nos. 6,610,651, 5,622,699 and 6,296,832, the complete disclosures of which are incorporated herein by reference. Molecules can be identified which home to cells, tissues or organs that are normal or that exhibit a pathological state, such as inflammation, or to pathological lesions, such as cancer, in a tissue or organ. In vivo panning comprises administering (by any route) a library of molecules to a subject, collecting an organ or tissue sample from the subject, and identifying the homing molecules using various methods well known in the art. Typically, the selected organ or tissue will be processed using a method such as HPLC, which can be used to obtain an enriched fraction of molecules having a defined range of molecular weights or polarity or the like from a complex mixture. The enriched fraction of molecules then can be further analyzed for the purposes of identifying cell, organ or tissue homing molecules using, for example, HPLC, mass spectrometry and gas chromatography. The libraries can be composed of naturally-occurring molecules and/or nonnaturally-occurring molecules and are made by methods well known in the art. See U.S. Pat. No. 6,610,651. These homing molecules can be conjugated to a PAC so that the PAC will be targeted to a desired target cell, tissue or organ. Also, a homing protein or peptide and a PAC could be expressed as a fusion protein using recombinant DNA techniques. The homing molecules can also be used to deliver genes to target cells, tissues and organs. Thus, a gene encoding a PAC (IPAC or EPAC) could be delivered into a target cell, tissue or organ using the homing molecules, where it could be expressed.

B. Therapeutic Methods and Pharmaceutical Products

The invention provides methods of treating diseases and conditions mediated by increased phosphorylation. An EPAC can be used to treat any such disease or condition. An IPAC should only be used to treat diseases and conditions, such as cancer, where cell death is desired or can be tolerated. The invention also provides pharmaceutical products comprising PACs.

Diseases and conditions mediated by increased phosphorylation include inflammation, inflammatory diseases and conditions, cancer, other proliferative disorders, autoimmune diseases, allergic reactions and other immune disorders.

Inflammation is a cascade of events through which the body responds to a variety of injuries, infections and stresses. Many of the phenomena characteristic of inflammation are associated with intensified signal transduction at the cellular and molecular levels. One important characteristic feature of cell signaling is phosphorylation. Enzymes, proteins, peptides and other molecules are activated by phosphorylation or dephosphorylation pathways. In many instances, when an activation event involves phosphorylation, it is followed by a counter-dephosphorylation step so that a pulse signal is transmitted as opposed to a continuous stimulus. A balance normally exists between the phosphorylases/kinases and the phosphatases. On a molecular level, inflammation can be viewed as an imbalance in favor of the kinases. Inflammation involves expression of kinases intracellularly and externalization or activation of kinases on the outer membrane of cells and in some cases, inhibition of phosphatases, resulting in increased kinase activity.

The inflammatory response is critical for stress response, fending off infections and healing wounds, but inflammation can also be damaging. Indeed, inflammation is an important component of the pathogenic process of many diseases and disorders. In addition, the presence of inflammation in many diseases, such as cancer, is indicative of a less favorable prognosis. Finally, in the extreme, inflammation may result in a life-threatening systemic response if not properly treated.

As noted above, the EPACs are substrates for phosphorylation by membrane-bound and/or circulating/soluble kinases, which are increased in inflammation. Phosphorylation of the EPACs reduces or prevents phosphorylation of extracellular and intracellular proteins, peptides and other compounds which, as a result of phosphorylation, would become participants in inflammatory processes. In particular, phosphorylation of the EPACs by membrane-bound kinases reduces or prevents signal transduction from the outside to the inside of cells. For these reasons, EPACs interfere with inflammatory processes and inhibit inflammation.

Specific inflammatory diseases and conditions treatable with the EPACs of the invention include acute respiratory distress syndrome, allergies, arthritis, asthma, autoimmune diseases (e.g, multiple sclerosis), bronchitis, cancer, Crohn's disease, cystic fibrosis, emphysema, endocarditis, gastritis, infections (bacterial, viral, yeast, fungal and parasitic), inflammatory bowel disease, inflammatory skin disorders, ischemia reperfusion, multiple organ dysfunction syndrome, multiple organ failure, nephritis, neurodegenerative diseases (e.g., Alzheimer's disease, amyotropic lateral sclerosis, Huntington's chorea, Parkinson's disease, senile dementia), pancreatitis, psoriasis, respiratory viral infections, sepsis, shock, systemic inflammatory response syndrome, trauma, ulcerative colitis and other inflammatory diseases, conditions and disorders.

Cancers can be treated with either EPACs and/or IPACs. As noted above, IPACs are preferably targeted so that they enter only cancer cells. Specific cancers treatable with the PACs of the invention include carcinomas, sarcomas, brain cancers, head and neck cancers, breast cancers, ovarian cancers, prostate cancers, gastric cancers, colon cancers, pancreatic cancers, bladder cancers, thyroid cancers, hepatic cancers, lung cancers, bone cancers, skin cancers, blood cancers, lymphomas and leukemias.

The other proliferative disorders include blood vessel proliferative disorders, mesangial cell proliferation disorders and fibrotic disorders. Blood vessel proliferative disorders include angiogenic diseases and conditions. An angiogenic disease or condition is a disease or condition involving, caused by, exacerbated by, or dependent on angiogenesis. Angiogenesis is the process of new blood vessel formation in the body. Specific angiogenic diseases and conditions treatable in accordance with the invention include neoplastic diseases (e.g., tumors (e.g., tumors of the bladder, brain, breast, cervix, colon, rectum, kidney, lung, ovary, pancreas, prostate, stomach and uterus) and tumor metastasis), benign tumors (e.g., hemangiomas, acoustic neuromas, neurofibromas, trachomas, and pyrogenic granulomas), hypertrophy (e.g., cardiac hypertrophy induced by thyroid hormone), connective tissue disorders (e.g., rheumatoid arthritis and atherosclerosis), psoriasis, ocular angiogenic diseases (e.g., diabetic retinopathy, retinopathy of prematurity, macular degeneration, corneal graft rejection, neovascular glaucoma, retrolental fibroplasia, and rubeosis), cardiovascular diseases, cerebral vascular diseases, endometriosis, polyposis, obesity, diabetes-associated diseases, hemophiliac joints, and immune disorders (e.g., chronic inflammation and autoimmunity). The neoplastic diseases may be treated with either EPACs and/or IPACs, as described above. The other angiogenic diseases and conditions are treated with EPACs. The EPACs of the invention can also be used to inhibit the vascularization required for embryo implantation, thereby providing a method of birth control.

Mesangial cell proliferative disorders refer to disorders brought about by abnormal proliferation of mesangial cells. Mesangial cell proliferative disorders include renal diseases, such as glomerulonephritis, diabetic nephropathy, malignant nephrosclerosis, thrombotic microangiopathy syndromes and glomerulopathies. Malignant mesangial cell proliferative disorders can be treated with EPACs and/or IPACs, and the remaining disorders are treated with EPACs.

Fibrotic disorders refer to the abnormal formation of extracellular matrices. Examples of fibrotic disorders include hepatic cirrhosis, pulmonary fibrosis and atherosclerosis. Fibrotic disorders are treated with EPACs.

Other proliferative disorders include hyperproliferative skin disorders, such as psoriasis, skin cancer and epidermal hyperproliferation. Psoriasis is characterized by inflammation, hyperproliferation of the epidermis and decreased differentiation of cells. Skin cancer can be treated with EPACs and/or IPACs, and the remaining disorders are treated with EPACs.

Autoimmune diseases treatable with the EPACs of the invention include multiple sclerosis. Other immune disorders treatable with the EPACs of the invention include transplant rejection.

In a preferred embodiment of the invention, the PACs will be used to treat skin diseases and conditions. Skin diseases and conditions treatable with an EPAC of the invention include a dermatitis, eczema, keratosis, elastosis, psoriasis, infections (e.g., measles and chicken pox), an acne, burns, sunburn, allergic reactions (e.g., rashes and hives), and any other inflammatory disease or condition. Skin cancers can be treated with either an EPAC and/or an IPAC, as described above.

In another preferred embodiment of the invention, the PACs will be used to treat diseases and conditions of the mouth. Mouth diseases and conditions treatable with an EPAC of the invention include leukoplakia, lichen plannus, infections and other inflammatory diseases and conditions, Mouth cancers can be treated with either an EPAC and/or an IPAC, as described above. Many other disease and conditions of the mouth, such as gingivits and periodontitis, will be typically be treated by, or under the supervision of; a dentist, and the treatment of these disease and conditions is described below in the section on oral care products and methods.

In yet another preferred embodiment of the invention, the EPACs will be used to treat diseases and conditions of, or involving, the mucous membranes. Such diseases and conditions include allergies, infections and inflammatory diseases and conditions.

To treat an animal suffering from a disease or condition mediated by increased phosphorylation, an effective amount of a PAC or a combination of PACs is administered to the animal. As noted above, EPAC(s) can be used to treat any such disease or condition. IPAC(s) should only be used to treat diseases and conditions, such as cancer, where cell death is desired or can be tolerated. Preferably, the animal is a mammal, such as a rabbit, goat, dog, cat, horse, bovine or human, most preferably a human.

Effective dosage forms, modes of administration and dosage amounts for the various PACs may be determined empirically, and making such determinations is within the skill of the art. It is understood by those skilled in the art that the dosage amount will vary with the particular PAC(s) employed, whether the PAC(s) is(are) being administered prophylactically or to treat an existing disease or condition, the specific disease or condition to be treated, the severity of the disease or condition, the route(s) of administration, the type(s) of compositions and/or devices used to administer the PAC(s), the rate of excretion of the PAC(s), the duration of the treatment, the identity of any other drugs being administered to the animal, the age, size and species of the animal, and like factors known in the medical and veterinary arts. In general, a suitable daily dose of a PAC of the present invention will be that amount of the compound which is the lowest effective dose to produce a therapeutic effect. If desired, the effective daily dose may be administered as two, three, four, five, six or more sub-doses, administered separately at appropriate intervals throughout the day. Administration of the PAC(s) should be continued until an acceptable response is achieved.

The PAC(s) of the present invention may be administered to an animal patient for treatment of a disease or condition mediated by increased phosphorylation by any suitable route of administration, including orally, nasally, rectally, vaginally, parenterally (e.g., intravenously, intraspinally, intraperitoneally, subcutaneously, or intramuscualarly), intracisternally, transdermally, transmucosally, intracranially, intracerebrally, and topically. The preferred routes of administration are topically, orally and locally. Examples of local administration include administration intracranially, into a tumor or cancerous lesion, intraocularly, into a lesion, nasally, vaginally, anally, into the lungs, into the gastrointestinal tract and into the mouth. IPACs will often have to be administered systemically to treat cancer. As noted above, when an IPAC is administered systemically, it is highly preferable that it be targeted so that it enters only or preferentially the selected cells, tissues or organs.

While it is possible for a PAC of the present invention to be administered alone, it is preferable to administer the PAC as a pharmaceutical formulation (composition). The pharmaceutical compositions of the invention comprise a PAC or a combination of PACs as active ingredient(s) in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the PACs of the present invention are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient (i.e., a PAC or combination of PACs) is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compound(s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical, transdermal or transmucosal administration of a compound of this invention include powders, sprays, ointments, pastes, creams, lotions, gels, solutions, patches, drops and inhalants. The active compound(s) may be mixed under sterile conditions with a pharmaceutically-acceptable carrier, and with any buffers, or propellants which may be required.

The ointments, pastes, creams and gels may contain, in addition to a compound or compound(s) of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound or compounds of this invention, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

The active ingredient (i.e., a PAC or combination of PACs of the invention) may also be delivered through the skin using conventional transdermal drug delivery systems, i.e., transdermal patches, wherein the active ingredient is typically contained within a laminated structure that serves as a drug delivery device to be affixed to the skin. In such a structure, the active ingredient is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active ingredient and any other materials that are present. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery devices may be fabricated using conventional techniques, known in the art, for example by casting a fluid admixture of adhesive, active ingredient and vehicle onto the backing layer, followed by lamination of the release liner. Similarly, the adhesive mixture may be cast onto the release liner, followed by lamination of the backing layer. Alternatively, the drug reservoir may be prepared in the absence of active ingredient or excipient, and then loaded by "soaking" in a drug/vehicle mixture.

The laminated transdermal drug delivery systems may, in addition, contain a skin permeation enhancer. That is, because the inherent permeability of the skin to some active ingredients may be too low to allow therapeutic levels of the drug to pass through a reasonably sized area of unbroken skin, it is necessary to coadminister a skin permeation enhancer with such drugs. Suitable enhancers are well known in the art.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery.

As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The PAC(s) of the invention may be administered alone or may be administered in combination with one or more other drugs, compounds or other materials. For instance, an EPAC can be administered in combination with one or more additional anti-inflammatory compounds, including steroids, non-steroid anti-inflammatory compounds (e.g., aspirin, ibuprofen, etc.), and those anti-inflammatory compounds described in U.S. patent application Ser. Nos. 09/678,202, 09/922,234, and 10/186,168, and PCT applications WO 01/25265, WO 02/11676 and WO 02/64620, the complete disclosures of which are incorporated herein by reference.

C. Excised Cells, Tissues and Organs

The EPACs of the invention can also be used to inhibit increased phosphorylation in a cell, tissue or organ that has been removed from an animal. Increased phosphorylation may be found in a cell, tissue or organ because of inflammation. To inhibit the increased phosphorylation in a tissue or an organ, the tissue or organ is contacted with a solution (e.g., by placing the tissue or organ in the solution and/or by perfusing an organ (e.g., a kidney) with the solution) containing an effective amount of an EPAC or combination of EPACs of the invention. Effective amounts of the EPAC(s) to include in such solutions can be determined empirically, and doing so is within the skill in the art. The harvested tissue or organ may subsequently be used for transplantation into a recipient or for research purposes (e.g., using a perfused liver to screen drugs). The EPACs of the invention can be used alone or can be used in combination with other compounds, drugs or materials.

Many suitable solutions for use with tissues and organs are known in which an EPAC or combination of EPACs of the invention could be used. See, e.g., Hauet et al., *J. Pharmacol. Exp. Ther.*, 297, 946-953 (2001); Hauet et al., *J. Pharmacol. Exp. Ther.*, 292, 254-260 (2000); Dunphy et al., *Am. J. Physiol.*, 276, H1591-H1598 (1999); Muhlbacher et al., *Transplant Proc.*, 31, 2069-2070 (1999); Watts et al., *J. Mol. Cell. Cardiol.*, 31, 1653-1666 (1999); Suzer et al., *Pharmacol. Res.*, 37, 97-101 (1998); Collins et al., *Kidney Int'l*, 42, Suppl. 38, S-197-S-202 (1992); Paller, *Ren. Fail.*, 14, 257-260 (1992); Baron et al., *J. Surg. Res.*, 51, 60-65 (1991); Hisatomi et al., *Transplantation*, 52, 754-755 (1991); Belzer et al., *Transplantation*, 45, 673-76 (1988); U.S. Pat. Nos. 4,798,824, 4,873,230, 4,879,283, 5,514,536, and 5,710,172; and PCT application WO 98/35551 (the disclosures of all of the foregoing are incorporated herein by reference).

For instance, a solution for flushing and cold storage of hearts is the Celsior™ solution (available from SangStat Medical Corp., Fremont, Calif.). Celsior™ solution contains:

TABLE A

| Component | Concentration |
| --- | --- |
| Mannitol | 60 mmol |
| Lactobionic Acid | 80 mmol |
| Glutamic Acid | 20 mmol |
| Histidine | 30 mmol |
| Calcium Chloride | 0.25 mmol |
| Potassium chloride | 15 mmol |
| Magnesium Chloride | 13 mmol |
| Sodium hydroxide | 100 mmol |
| Reduced Glutathione | 3 mmol |
| Water For Injection | Up to 1 liter |

The accepted standard solution for preservation of kidneys is the University Of Wisconsin solution (available from Barr Laboratories under tradename ViaSpan®) which has the following composition:

TABLE B

| Component | Concentration | Function |
|---|---|---|
| Raffinose | 30 mM (17.83 g/L) | Impermeant: suppression of hypothermic cell swelling |
| Lactobionic acid | 100 mM (35.83 g/L) | Impermeant: suppression of hypothermic cell swelling |
| Pentafraction (hydroxyethyl starch) | 50 g/L | Colloid: reduction of interstitial edema and endothelial cell swelling |
| Glutathione | 3 mM (0.992 g/L) | Antioxidant |
| Allopurinol | 1 mM (0.136 g/L) | Inhibition of xanthine oxidase activity and purine metabolism/ reduction of oxygen free radicals |
| Adenosine | 5 mM (1.34 g/L) | Restoration of high energy phosphate |
| Potassium phosphate | 25 mM (3.4 g/L) | pH buffer: maintenance of intracellular sodium and potassium concentrations: restoration of high energy phosphate |
| Magnesium sulfate | 5 mM (1.23 g/L) | Preservation of intracellular magnesium concentration |
| Potassium hydroxide | 100 mM (5.61 g/L) | Maintenance of intracellular sodium and potassium concentrations |
| Sodium hydroxide | 27 mM | Maintenance of intracellular sodium and potassium concentrations |

Solution is pH adjusted to 7.4 with either sodium hydroxide or hydrochloric acid.
Final: Sodium = 29 mM; Potassium = 125 mM; mOsm/L = 320 ± 10
Immediately prior to use, to formulate the final solution, aseptically add: Penicillin G 200,000 units, regular insulin 40 units, and dexamethasone 16 mg.

An EPAC or combination of EPACs of the invention could be used in either of these two solutions, variations of these solutions, or in one of the other numerous solutions known in the art or which will be developed. The EPAC(s) may be included in the solution or supplied separately (e.g., in lyophilized form) and added at the time of use.

Cells isolated from an animal can be stored or cultured in a medium containing an effective amount of an EPAC or combination of EPACs of the invention. Many suitable media are known. Effective amounts of the EPACs to include in the medium can be determined empirically, and doing so is within the skill in the art. The EPAC(s) may be included in the medium or supplied separately (e.g., in lyophilized form) and added at the time of use. The cells may be administered to a recipient in need thereof (e.g., for gene therapy) or may be used for research purposes.

The invention further provides a kit for inhibiting increased phosphorylation in a cell, a tissue or organ that has been removed from an animal. The kit is a packaged combination of one or more containers holding reagents and other items useful for preserving harvested cells, tissues or organs. The kit comprises a container holding one or more EPACs of the invention. Suitable containers include bottles, bags, vials, test tubes, syringes, and other containers known in the art. For instance, the kit may comprise a vial containing lyophilized EPAC(s). The kit may also contain other items which are known in the art and which may be desirable from a commercial and user standpoint, such as a container for the cells, tissue or organ, diluents, buffers, empty syringes, tubing, gauze pads, disinfectant solution, etc. The kits will also include instructions for using the kit to contact a cell, tissue or organ with the EPAC(s) contained in the kit.

D. Oral Care Products and Methods

The EPAC(s) of the invention may also be administered to an animal as oral care products. Oral care products include oral care compositions and oral care devices. Preferred EPACs for use in the oral care products of the invention are phosvitins and caseins which are at least partially dephosphorylated.

Oral care compositions of the invention include washes, rinses, gargles, solutions, drops, emulsions, suspensions, liquids, pastes, gels, ointments, creams, sprays, powders, tablets, gums, lozenges, mints, films, patches, and tooth whitening compositions. Oral care compositions of the invention include compositions intended for use by consumers and patients and compositions intended for use by dental professionals (e.g., dental hygienists, dentists and oral surgeons).

The oral care compositions of the invention will comprise an EPAC or EPACs of the invention as active ingredient(s) in admixture with one or more pharmaceutically-acceptable carriers. The oral care compositions of the invention may also comprise one or more other acceptable ingredients, including other active compounds and/or other ingredients conventionally used in oral care compositions. Each carrier and ingredient must be "acceptable" in the sense of being compatible with the other ingredients of the formulation and not injurious to the animal.

Suitable ingredients, including pharmaceutically-acceptable carriers, for use in oral care compositions, and methods of making and using oral care compositions, are well known in the art. See, e.g., U.S. Pat. Nos. 4,847,283, 5,032,384, 5,043,183, 5,180,578, 5,198,220, 5,242,910, 5,286,479, 5,298,237, 5,328,682, 5,407,664, 5,466,437, 5,707,610, 5,709,873, 5,738,840, 5,817,295, 5,858,408, 5,876,701, 5,906,811, 5,932,193, 5,932,191, 5,951,966, 5,976,507, 6,045,780, 6,197,331, 6,228,347, 6,251,372, and 6,350,438, PCT applications WO 95/32707, WO 96/08232 and WO 02/13775, and EP applications 471,396, the complete disclosure of all of which are incorporated herein by reference. Conventional ingredients used in oral care compositions include water, alcohols, humectants, surfactants, thickening agents, abrasives, flavoring agents, sweetening agents, antimicrobial agents, anti-caries agents, anti-plaque agents, anti-calculus agents, pH-adjusting agents, and many others.

The water used in oral care compositions should preferably be of low ion content. It should also be free of organic impurities.

The alcohol must be nontoxic. Preferably the alcohol is ethanol. Ethanol is a solvent and also acts as an antibacterial agent and as an astringent.

Humectants suitable for use in oral care compositions include edible polyhydric alcohols, such as glycerol, sorbitol, xylitol, butylene glycol, polyethylene glycol, propylene glycol, mannitol and lactitol. Humectants help keep oral care compositions, such as pastes, from hardening upon exposure to air, give oral care compositions a moist feel to the mouth, and may impart desirable sweetness.

Surfactants include anionic, nonionic, amphoteric, zwitterionic and cationic synthetic detergents. Anionic surfactants include the water-soluble salts of alkyl sulfates having 8-20 carbon atoms in the alkyl radical (such as sodium alkyl sulfate), the water-soluble salts of sulfonated monoglycerides of fatty acids having from 8-20 carbon atoms (such as sodium lauryl sulfate and sodium coconut monoglyceride sulfonates), sarcosinates (such as sodium and potassium salts of lauroyl sarcosinate, myristoyl sarcosinate, palmitoyl sarcosinate, stearoyl sarcosinate and oleoyl sarcosinate), taurates, higher alkyl sulfoacetates (such as sodium lauryl sulfoacetate), isethionates (such as sodium lauroyl isethionate), sodium laureth carboxylate, sodium dodecyl benezesulfonate, and mixtures of the foregoing. Preferred are the sarcosinates since they inhibit acid formation in the mouth due to carbohydrate breakdown. Nonionic surfactants include poloxamers (sold under the tradename Pluronic), polyoxyethylene sorbitan esters (sold under the tradename Tween), fatty alcohol ethoxylates, polyethylene oxide condensates of alkyl phenols, products derived from the condensation of ethylene oxide with fatty acids, fatty alcohols, fatty amides, polyhydric alcohols, and polypropyleneoxide, ethylene oxide condensates of aliphatic alcohols, long-chain tertiary amine oxides, long-chain tertiary phosphine oxides, long-chain dialkyl sulfoxides, and mixtures of such materials. Amphoteric surfactants include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials. Zwitterionic surfactants include derivatives of aliphatic quaternary ammonium, phosphonium and sulfonium compounds in which the aliphatic radical can be a straight or branched chain and wherein one of the aliphatic substituents contains about 8-18 carbon atoms and one contains an anionic water-solubilizing group (such as carboxy, sulfonate, sulfate, phosphate or phosphonate). Cationic surfactants include aliphatic quaternary ammonium compounds having one long alkyl chain containing about 8-18 carbon atoms (such as lauryl trimethylammonium chloride, cetylpyridinium chloride, cetyltrimethylammonium bromide, diisobuytylphenoxyethyldimethylbenzylammonium chloride, coconut alkyltrimethylammonium nitrite, cetylpyridinium fluoride). Certain cationic surfactants can also act as antimicrobials.

Thickening agents include carboxyvinyl polymers, polyvinylpyrrolidone, polyacrylates, carrageenan, cellulose derivatives (e.g., hydroxypropyl cellulose, hydroxypropyl methyl cellulose, methyl cellulose, and hydroxyethyl cellulose), laponite, water-soluble salts of cellulose ethers (such as sodium carboxymethylcellulose and sodium carboxymethyl hydroxyethyl cellulose), natural gums (such as gum karaya, xanthan gum, gum arabic and gum tragacanth), polymeric polyether compounds (such as polyethylene oxide and polypropylene oxide), homopolymers of acrylic acid crosslinked with an alkyl ether of pentaerythritol, alkyl ether of sucrose, carbomers (sold under the tradename Carbopol®), starch, copolymers of lactide and glycolide monomers (the copolymer having an average molecular weight of about 1,000-120,000), colloidal magnesium aluminum silicate and finely divided silica. Thickening agents will be added in amounts sufficient to give a desired consistency to an oral care composition.

Abrasives include silicas (including gels and precipitates), aluminas, calcium carbonates, calcium phosphates, dicalcium phosphates, tricalcium phosphates, hydroxyapatites, calcium pyrophosphates, trimetaphosphates, insoluble polymetaphosphates (such as insoluble sodium polymetaphosphate and calcium polymetaphosphate), magnesium carbonates, magnesium oxides, resinous abrasive materials (such as particulate condensation products of urea and formaldehyde), particulate thermosetting polymerized resins (suitable resins include melamines, phenolics, ureas, melamine-ureas, melamine-formaldehydes, urea-formaldehydes, melamine-urea-formaldehydes, cross-linked epoxides and cross-linked polyesters), and combinations of the foregoing. Silica abrasives are preferred because they provide excellent dental cleaning and polishing performance without unduly abrading tooth enamel or dentine.

Flavoring agents include peppermint, oil, spearmint oil, wintergreen oil, clove, menthol, dihydroanethole, estragole, methyl salicylate, eucalyptol, *cassia,* 1-menthyl acetate, sage, eugenol, parsley oil, menthone, oxanone, alpha-irisone, alpha-ionone, anise, marjoram, lemon, orange, propenyl guaethol, cinnamon, vanillin, ethyl vanillin, thymol, linalool, limonene, isoamylacetate, benzaldehyde, ethylbutyrate, phenyl ethyl alcohol, sweet birch, cinnamic aldehyde, cinnamaldehyde glycerol acetal (known as CGA), and mixtures of the foregoing.

Sweetening agents include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame, cyclamate salts, and mixtures of the foregoing.

In addition to the flavoring and sweetening agents, the oral care compositions may include coolants, salivating agents, warming agents and numbing agents as optional ingredients. Coolants include carboxamides, menthol, paramenthan carboxamides, isopropylbutanamide, ketals, diols, 3-1-menthoxypropane-1,2-diol, menthone glycerol acetal, menthyl lactate, and mixtures thereof. Salivating agents include Jambu® (manufactured by Takasago). Warming agents include *capsicum* and nicotinate esters (such as benzyl nicotinate). Numbing agents include benzocaine, lidocaine, clove bud oil and ethanol.

Antibacterial and anti-plaque agents include triclosan, sanguinarine and sanguinaria, quaternary ammonium compounds, cetylpyridinium chloride, tetradecylpyridinium chloride and N-tetradecyl-4-ethylpyridinium chloride, benzalkonium chloride, bisquanides, chlorhexidine, chlorhexidine digluconate, hexetidine, octenidine, alexidine, halogenated bisphenolic compounds, 2,2'-methylenebis-(4-chloro-6-bromophenol), 5-chloro-2-(2,4-dichlorophenoxy)-phenol, salicylanilide, domiphen bromide, delmopinol, octapinol, other piperadino derivatives, nicin, zinc stannous ion agents, antibiotics (such as augimentin, amoxicillin, tetracycline, doxycycline, minocycline, and metronidazole), analogs and salts of the foregoing, and mixtures of the foregoing.

Anti-caries agents include sodium fluoride, stannous fluoride, potassium fluoride, amine fluorides, indium fluoride, sodium monofluorophosphate, calcium lactate, calcium glycerophosphates, strontium salts, and strontium polyacrylates.

Anti-calculus agents include pyrophosphate salts such as dialkali metal pyrophosphate salts and tetraalkali metal pyrophosphate salts (e.g., disodium dihydrogen pyrophosphate, tetrasodium pyrophosphate and tetrapotassium pyrophosphate, in their hydrated and unhydrated forms). Other anti-calculus agents which can be used instead of, or in addition to, the pyrophosphate salts include synthetic anionic polymers (such as polyacrylates and copolymers of maleic anhydride or acid and methyl vinyl ether), polyaminopropane sulfonic acid, zinc citrate trihydrate, polyphosphates (such as tripolyphosphate and hexametaphosphate), polyphosphonates (such as disodium ethane-1-hydroxy-1,1-diphosphonate (EHDP), methanedisphosphonic acid, and 2-phosphonobutane-1,2,4-tricarboxylic acid), and polypeptides (such as polyaspartic acid and polyglutamic acid).

The pH of the oral care compositions of the invention should preferably not be acidic. Thus, the pH of the oral care compositions of the invention should be greater than about 6.5, preferably from about 7.0 to about 8.5, more preferably from about 7.2 to about 7.6. Thus, a pH-adjusting agent and/or a buffering agent or agents may need to be included in the oral care compositions. The pH-adjusting agent may be any compound or mixture of compounds that will achieve the desired pH. Suitable pH-adjusting agents include organic and inorganic acids and bases, such as benzoic acid, citric acid, potassium hydroxide, and sodium hydroxide. Buffering agents include acetate salts, borate salts, carbonate salts, bicarbonate salts (e.g., an alkali metal bicarbonate, such as sodium bicarbonate (also known as baking soda)), gluconates, tartrates, sulfates, citrates (such as sodium citrate), benzoate salts, nitrate salts (such as sodium and potassium nitrate), and combinations of the foregoing as needed to achieve and maintain the desired pH.

In addition to the one or more EPACs, the oral care compositions of the invention may include one or more additional anti-inflammatory agents, antioxidants and/or metal-binding compounds.

Suitable anti-inflammatory agents include ibuprofen, flurbiprofen, ketoprofen, aspirin, kertorolac, naproxen, indomethacin, piroxicam, meclofenamic acid, steroids, and mixtures of the foregoing.

Suitable antioxidants include superoxide dismutase, catalase, glutathione peroxidase, ebselen, glutathione, cysteine, N-acetyl cysteine, penicillamine, allopurinol, oxypurinol, ascorbic acid, α-tocopherol, Trolox (water-soluble α-tocopherol), vitamin A, β-carotene, fatty-acid binding protein, fenozan, probucol, cyanidanol-3, dimercaptopropanol, indapamide, emoxipine, dimethyl sulfoxide, and others. See, e.g., Das et al., *Methods Enzymol.*, 233, 601-610 (1994); Stohs, *J. Basic Clin. Physiol. Pharmacol.*, 6, 205-228 (1995).

Suitable metal-binding compounds include metal-binding peptide and/or non-peptide chelators. Metal-binding peptides and non-peptide chelators are known in the art. Preferred are those metal-binding peptides and non-peptide chelators described in PCT applications WO 01/25265 and WO 02/64620, the complete disclosures of which are incorporated herein by reference. Additional metal-binding compounds are polyethylenepolyamines, such as tetraethylenetriamine (trientine).

The oral care compositions of the invention may advantageously contain a protease inhibitor to prevent degradation of the EPACs and/or for an additional therapeutic effect (certain proteases are involved in inflammatory processes and others have been implicated in tissue breakdown in the mouth). Suitable protease inhibitors include metalloproteinase and serine protease inhibitors, such as those described in U.S. Pat. Nos. 6,403,633, 6,350,438, 6,066,673, 5,622,984, and 4,454,338, the complete disclosures of which are incorporated herein by reference.

Many other ingredients are known that may be incorporated into oral care compositions. These include suspending agents (such as a polysaccharide—see U.S. Pat. No. 5,466,437), polymeric compounds which can enhance the delivery of active ingredients (such as copolymers of polyvinylmethylether with maleic anhydride and those delivery enhancing polymers described in DE 942,643 and U.S. Pat. No. 5,466,437), materials which allow for a strong and continuing adherence of the oral care composition to the tissues of the mouth, thereby providing for a protracted topical therapeutic effect (such as natural gums, plant extracts, animal extracts (e.g., gelatin), natural and synthetic polymers, and starch derivatives; see, e.g., U.S. Pat. Nos. 5,032,384, 5,298,237, and 5,466,437), oils, waxes, silicones, coloring agents (such as FD&C dyes), color change systems, preservatives (such as methylparaben, propylparaben, and sodium benzoate), opacifying agents (such as titanium dioxide), plant extracts, solubilizing agents (such as propylene glycol; see, e.g., U.S. Pat. No. 5,466,437), enzymes (such as dextranase and/or mutanase, amyloglucosidase, glucose oxidase with lactoperoxidase, and neuraminidases), synthetic or natural polymers, tooth whitening agents (such from about 0.1% to about 10% by weight of a peroxygen compound; see additional discussion of tooth whitening compositions below), an alkali metal bicarbonate (such as sodium bicarbonate (also known as baking soda), generally present at from about 0.01% to about 30% by weight), desensitizers (such as potassium salts (e.g., potassium nitrate, potassium citrate, potassium chloride, potassium tartrate, potassium bicarbonate, and potassium oxalate) and strontium salts), analgesics (such as lidocaine or benzocaine), anti-fungal agents, antiviral agents, etc.

It will be appreciated that a wide variety of different oral care compositions can be prepared utilizing the above described ingredients and other ingredients known in the art or which will be developed. It is within the skill in the art to chose appropriate ingredients and combinations of ingredients and to determine an effective amount of the EPAC(s) of the invention to include in a particular oral care composition, given the knowledge in the art and the guidance provided herein.

What follows are a few examples of oral care compositions into which a EPAC or a combination of EPACs could be incorporated. It will be understood by those skilled in the art that additional types of oral care compositions and additional oral care compositions having different ingredients and/or different amounts of ingredients can be prepared utilizing the knowledge and skill in the art and the guidance provided herein.

Dentrifices include toothpastes, tooth gels, tooth powders and liquid dentrifices. Toothpastes and tooth gels generally include a dental abrasive, a surfactant, a thickening agent, a humectant, a flavoring agent, a sweetening agent, a coloring agent and water. Toothpastes and tooth gels may also include opacifying agents, anti-caries agents, anti-calculus agents, tooth whitening agents, and other optional ingredients. Typically, a toothpaste or tooth gel will contain from about 5% to about 70%, preferably from about 10% to about 50%, of an abrasive, from about 0.5% to about 10% of a surfactant, from about 0.1% to about 10% of a thickening agent, from about 10% to about 80% of a humectant, from about 0.04% to about 2% of a flavoring agent, from about 0.1% to about 3% of a sweetening agent, from about 0.01% to about 0.5% of a coloring agent, from about 0.05% to about 0.3% of an anti-caries agent, from about 0.1% to about 13% of an anti-calculus agent, and from about 2% to about 45% water. Tooth powders of course contain substantially all non-liquid components and typically contain from about 70% to about 99% abrasive. Liquid dentrifices may comprise water, ethanol, a humectant, a surfactant, a thickening agent, an abrasive (if an abrasive is included, a suspending agent (e.g., a high molecular weight polysaccharide) must be included; see U.S. Pat. No. 5,466,437), an antibacterial agent, an anti-caries agent, a flavoring agent and a sweetening agent. A typical liquid dentrifice will comprise from about 50% to about 85% water, from about 0.5% to about 20% ethanol, from about 10% to about 40% of a humectant, from about 0.5% to about 5% of a surfactant, from about 0.1% to about 10% of a thickening agent, and may contain from about 10% to about 20% of an abrasive, from about 0.3% to about 2% of a suspending agent, from about 0.05% to about 4% of an antibacterial agent, from about 0.0005% to about 3% of an anti-caries agent, from about 0.1% to about 5% of a flavoring agent, and from about 0.1% to about 5% of a sweetening agent.

Gels include dentrifice gels (see description above), non-abrasive gels and subgingival gels. Non-abrasive gels and subgingival gels generally include a thickening agent, a humectant, a flavoring agent, a sweetening agent, a coloring agent, and water. Such gels may also include one or more anti-caries agents and/or anti-calculus agents. Typically, such a gel will contain from about 0.1% to about 20% of a thickening agent, from about 10% to about 55% of a humectant, from about 0.04% to about 2% of a flavoring agent, from about 0.1% to about 3% of a sweetening agent, from about 0.01% to about 0.5% of a coloring agent, and the balance water. Such gels may also contain from about 0.05% to about 0.3% of an anti-caries agent and from about 0.1% to about 13% of an anti-calculus agent.

Creams generally include a thickening agent, a humectant and a surfactant, and may include a flavoring agent, a sweetening agent, a coloring agent. Typically, a cream will contain from about 0.1% to about 30% of a thickening agent, from about 0% to about 80% of a humectant, from about 0.1% to about 5% of a surfactant, from about 0.04% to about 2% of a flavoring agent, from about 0.1% to about 3% of a sweetening agent, from about 0.01% to about 0.5% of a coloring agent, and from about 2% to about 45% of water.

Ointments suitable for oral use are described in, e.g., U.S. Pat. Nos. 4,847,283, 5,855,872 and 5,858,408, the complete disclosures of which are incorporated herein by reference. Ointments generally include one or more of the following: fats, oils, waxes, parafins, silicones, plastibase, alcohols, water, humectants, surfactants, thickening agents, talc, bentonites, zinc oxide, aluminum compounds, preservatives, antiviral compounds, and other ingredients. For instance, the ointment may comprise from about 80% to about 90% petrolatum and from about 10% to about 20% ethanol or propylene glycol. As another example, the ointment may comprise about 10% petrolatum, about 9% lanolin, about 8% talc, about 32% cod liver oil, and about 40% zinc oxide. As a third example, the ointment may comprise from about 30% to about 45% water, from about 10% to about 30% oil (e.g., petrolatum or mineral oil), from about 0.1% to about 10% emulsifier (e.g., wax NF), from about 2% to about 20% humectant (e.g., propylene glycol), from about 0.05% to about 2% preservatives (e.g., methyl paraben and propyl paraben), and from about 10% to about 40% sterol alcohol.

Mouthwashes, rinses, gargles and sprays generally include water, ethanol, and/or a humectant, and preferably also include a surfactant, a flavoring agent, a sweetening agent, and a coloring agent, and may include a thickening agent and one or more anti-caries agents and/or anti-calculus agents. A typical composition contains from about 0% to about 80% of a humectant, from about 0.01% to about 7% of a surfactant, from about 0.03% to about 2% of a flavoring agent, from about 0.005% to about 3% of a sweetening agent, from about 0.001% to about 0.5% of a coloring agent, with the balance being water. Another typical composition contains from about 5% to about 60%, preferably from about 5% to about 20%, ethanol, from about 0% to about 30%, preferably from about 5% to about 20%, of a humectant, from about 0% to about 2% emulsifying agents, from about 0% to about 0.5% of a sweetening agent, from about 0% to about 0.3% of a flavoring agent, and the balance water. A further typical composition contains from about 45% to about 95% water, from about 0% to about 25% ethanol, from about 0% to about 50% of a humectant, from about 0.1% to about 7% of a surfactant, from about 0.1% to about 3% of a sweetening agent, from about 0.4% to about 2% of a flavoring agent, and from about 0.001% to about 0.5% of a coloring agent. These compositions may also comprise from about 0.05% to about 0.3% of an anti-caries agent, and from about 0.1% to about 3% of an anti-calculus agent Solutions generally include water, a preservative, a flavoring agent, and a sweetening agent, and may include a thickening agent and/or a surfactant. Typically, solutions contain from about 85% to about 99% water, from about 0.01% to about 0.5% of a preservative, from about 0% to about 5% of a thickening agent, from about 0.04% to about 2% of a flavoring agent, from about 0.1% to about 3% of a sweetening agent, and from about 0% to about 5% of a surfactant.

Lozenges and mints generally include a base, a flavoring agent and a sweetening agent. The base may be a candy base (hard sugar candy), glycerinated gelatin or a combination of sugar with sufficient mucilage to give it form. See U.S. Pat. No. 6,350,438 and Remington, *The Science And Practice Of Pharmacy*, 19$^{th}$ edition (1995). Lozenge compositions also typically include one or more fillers (e.g., a compressible sugar) and lubricants.

Chewing gums, chewable tablets and chewable lozenges are described in U.S. Pat. Nos. 6,471,991, 6,296,868, 6,146,661, 6,060,078, 5,869,095, 5,709,873, 5,476,647, and 5,312,626, PCT applications WO 84/04453 and WO 99/02137, and Lieberman et al., *Pharmaceutical Dosage Forms*, 2$^{nd}$ ed. (1990), the complete disclosures of which are incorporated here in by reference.

As one example, a compressed chewable tablet comprises a water-disintegratable, compressible carbohydrate (such as mannitol, sorbitol, maltitol, dextrose, sucrose, xylitol, lactose and mixtures thereof), a binder (such as cellulose, cellulosic derivatives, polyvinyl pyrrolidone, starch, modified starch and mixtures thereof), and, optionally, a lubricant (such as magnesium stearate, stearic acid, talc, and waxes), sweetening, coloring and flavoring agents, a surfactant, a preservative, and other ingredients. All of the ingredients, including the EPAC(s) of the invention, are dry blended and compressed into a tablet.

As another example, a chewable tablet may comprise a core surrounded by an outer layer wrapping the core. The core may comprise a EPAC or EPACs of the invention and, optionally, other active ingredients in a jelly base or a chewable base. The outer layer may be a chewable base. The jelly base may comprise pectin, sorbitol, maltitol, isomalt, liquid glucose, sugar, citric acid and/or a flavoring agent. The chewable base of the core or outer layer may be a gum, soft candy, nougat, caramel or hard candy. The tablets are formed by extrusion of the core and outer layer to form a rope, followed by cutting the rope into tablets.

Chewing gum compositions generally include a gum base, a flavoring agent and a sweetening agent. Suitable gum bases include jelutong, rubber, latex, chicle, and vinylite resins, desirably with conventional plasticizers or softeners. Plasticizers include triacetin, acetyl tributyl citrate, diethyl sebacetate, triethyl citrate, dibutyl sebacetate, dibutyl succinate, diethyl phthalate and acetylated monoglycerides. Typically, chewing gum compositions contain from about 50% to about 99% gum base, from about 0.4% to about 2% of a flavoring agent and from about 0.01% to about 20% of a sweetening agent. The EPAC(s) of the invention and other active ingredients may be incorporated into a gum base by, e.g., stirring them into a warm gum base or coating them onto the outer surface of the gum base.

Films and sheets, and gels which form solids in the mouth, made of lactide/glycolide copolymers are described in U.S. Pat. Nos. 5,198,220, 5,242,910 and 6,350,438. Another polymer film suitable for use in the mouth is described in PCT application WO 95/32707. Patches that adhere to hard dental surfaces, such as teeth and dentures, and which degrade in the mouth, are described in U.S. Pat. No. 6,197,331. All of these materials slowly release active agents contained in them into the mouth, Other compositions (including pastes, gels, ointments, liquids and films) providing for slow release of active agents are also known. See, e.g., U.S. Pat. Nos. 5,032,384, 5,298,237, 5,466,437, 5,709,873, and 6,270,781.

Tooth whitening compositions will comprise a tooth whitening agent. Tooth whitening agents include peroxides, percarbonates and perborates of the alkali and alkaline earth metals or complex compounds containing hydrogen peroxide. Tooth whitening agents also include peroxide salts of the alkali or alkaline earth metals. The most commonly used tooth whitening agent is carbamide peroxide. Other commonly used tooth whitening agents are hydrogen peroxide, peroxyacetic acid and sodium perborate. These tooth whitening agents liberate active oxygen and hydrogen peroxide. Tooth whitening agents can be present in tooth whitening compositions at a concentration of from about 0.1% to about 90%; typically, the concentration of carbamide peroxide in tooth whitening compositions is from about 10% to about 25%.

Many tooth whitening compositions are known in the art, including aqueous solutions, gels, pastes, liquids, films, strips, one-part systems, two-part systems, compositions that require activation of the tooth whitening agent (e.g., by inclusion of a radiant-energy or heat-energy absorbing substance, such as substantially conjugated hydrocarbons, which activates the bleaching agent when irradiated), etc. See, e.g., U.S. Pat. Nos. 5,302,375, 5,785,887, 5,858,332, 5,891,453, 5,922, 307, 6,322,773, 6,419,906, and PCT applications WO 99/37236, WO 01/89463 and WO 02/07695, the complete disclosures of which are incorporated herein by reference. Also, many other oral care compositions (e.g., toothpastes) and devices (e.g., dental flosses) comprise a tooth whitening agent.

The use of tooth whitening compositions, or of one of the many oral care compositions and devices which comprise a tooth whitening agent, results in the production of reactive oxygen species (ROS) and can cause inflammation of the tissues of the mouth. Incorporation of an EPAC or EPACs in tooth whitening compositions or other oral care compositions and devices comprising a tooth whitening agent will reduce or prevent the inflammation and should also reduce the production of ROS (as noted above, once phosphorylated, the EPACs bind metal ions and, as a result, can reduce the production of ROS). The inclusion of a EPAC or EPACs in such compositions may also result in more effective whitening, since hydrogen peroxide (which is responsible for the whitening of teeth by the hydrogen peroxide-type whitening agents and which is converted into hydroxyl radicals in the presence of metal ions) may not be converted into hydroxyl radicals (because of the binding of metal ions by phosphorylated EPACs) and will, therefore, remain active longer. Alternatively, an oral care composition or device comprising an EPAC or EPACs can be used before or after the tooth whitening composition or oral care composition or device comprising a tooth whitening agent to reduce or prevent the inflammation and, possibly, the production of ROS.

For instance, teeth are commonly whitened by applying a tooth whitening composition to the teeth by means of a dental tray or trough. An EPAC or EPACs of the invention could be incorporated into the tooth whitening composition that is used in the tray or trough. Alternatively, a separate composition comprising an EPAC or EPACs of the invention could be applied to the teeth in a cleaned or different tray or trough after the application of the tooth whitening composition is completed. In a further alternative, a wash or rinse comprising an EPAC or EPACs of the invention could be used to rinse the mouth before and/or after the application of the tooth whitening composition.

A recently developed product for applying a tooth whitening composition to the teeth is a flexible strip. See, e.g., U.S. Pat. Nos. 5,891,453 and 6,419,906. An EPAC or EPACs could be incorporated into such strips. For instance, the EPAC(s) could be incorporated into the tooth whitening composition, which is then applied to the strips, or a solution, gel or other composition comprising the EPAC(s) could be separately applied to the strips, either during their manufacture or just prior to use by the patient. In yet another alternative, strips comprising a tooth whitening composition and strips comprising the EPAC(s) could both be supplied to the patient and would be used sequentially.

The oral care compositions of the invention may comprise a single phase or a plurality of phases. A plurality of phases will be used, e.g., where some of the ingredients are incompatible, some of the ingredients are unstable, or the ingredients are best combined at the time of use. Thus, one of the phases will include some of the ingredients, and the remainder of the ingredients will be contained in one or more additional phases. The plurality of phases may be a plurality of separate compositions, in which case the plurality of phases will be provided in a plurality of separate containers or in a plurality of compartments in a single container, and the plurality of phases will be combined at the time of use. As an alternative, the plurality of phases may be formed by encapsulating some of the ingredients, in which case the plurality of phases may all be contained in a single container. Multi-phase oral care compositions are described in, e.g., U.S. Pat. Nos. 5,302,375, 5,906,811, 5,976,507, 6,228,347 and 6,350,438 and PCT application number WO 99/37236.

The invention also provides oral care devices comprising an EPAC or EPACs. Oral care devices of the invention include devices intended for use by consumers and patients and devices intended for use by dental professionals (e.g., dental hygienists, dentists and oral surgeons).

The oral care devices of the invention include surgical materials (such as sutures and sponges), flosses, tapes, chips, strips, fibers, a toothpick or rubber tip, dental implants and dental appliances (such as trays and troughs that fit over and cover the teeth and, optionally, the periodontal tissue) having an EPAC or EPACs adhered to, absorbed into, bound to, attached to, entrapped in, coated onto, or otherwise incorporated into, them. See, e.g., U.S. Pat. Nos. 5,709,873, 5,863, 202, 5,891,453, 5,967,155, 5,972,366, 5,980,249, 6,026,829, 6,080,481, 6,102,050, 6,350,438, 6,419,906, PCT application WO 02/13775, and EP application 752833, which describe such oral care devices and methods of incorporating compounds into them (the complete disclosures of all of these patents and applications are incorporated herein by reference). For instance, an EPAC or EPACs can be incorporated into a binder (e.g., a wax or polymer) and coated onto dental floss, dental floss can be soaked in a bath of a liquid containing an EPAC or EPACs to impregnate or coat the floss with the compound(s), an EPAC or EPACs in solid (e.g., freeze-dried) form can be incorporated into a polymer film suitable for application to the teeth, an EPAC or EPACs in a solution or gel can be applied to a flexible strip suitable for application to teeth, or a suture or other surgical material can be soaked in a solution containing an EPAC or EPACs followed by removal of the solvent so that the compound(s) become associated with (bound to, entrapped in, coated onto, etc.) the suture or surgical material. See, e.g., U.S. Pat. Nos. 5,891,453, 5,967, 155, 5,972,366, 6,026,829, 6,080,481, 6,102,050, and 6,419, 906.

Also included within the scope of the invention are oral care products for animals, such as foods, chews, and toys. Suitable products are described in U.S. Pat. No. 6,350,438.

An EPAC or EPACs of the invention can be used to treat a tissue of an animal's mouth to inhibit increased phosphorylation. "Mouth" is used herein to mean the cavity bounded externally by the lips and internally by the pharynx that encloses the tongue, gums and teeth. Thus, the tissues of the mouth include the lips, tongue, gums, buccal tissue, palate and teeth. A single tissue, a plurality of tissues, a portion of one or more tissues, all or substantially all of the tissues of the mouth, or combinations of the foregoing, may be treated according to the invention.

To treat a tissue of the mouth, the tissue is contacted with an EPAC or EPACs of the invention. For instance, the tissue may be contacted with an oral care composition comprising the EPAC(s). Methods of contacting tissues of the mouth with oral care compositions are well known in the art. Suitable methods include rinsing the tissue with a solution (e.g., a mouthwash, rinse, spray, liquid dentrifice, or other solution), brushing the teeth with a dentrifice (e.g., a toothpaste, tooth gel, or powder), applying a non-abrasive solution, gel, paste, cream or ointment directly to the tissue (with or without the use of an applicator), chewing gum, chewing or sucking a lozenge, mint or tablet, and many other means of topical application. Suitable applicators for applying oral care compositions, such as solutions, gels, pastes, creams and ointments, to a tissue include a swab, a stick, a plastic paddle, a dropper, a syringe, a strip (such as those described in U.S. Pat. Nos. 5,891,453 and 6,419,906), a finger, or a dental tray or appliance (such as those shown in U.S. Pat. Nos. 5,863,202 and 5,980,249 and EP application 752833) which allows for immersion of the teeth and, optionally, the periodontal tissue in, e.g., a gel or solution. In addition, to treat a tissue of the mouth, the tissue may be contacted with an oral care device comprising the EPAC(s). Methods of contacting tissues of the mouth with oral care devices are well known in the art. For instance, sutures can be used to close a surgical wound or a wound resulting from a tooth extraction, dental floss can be used to floss the teeth, etc.

The treatment of the tissue can be prophylactic treatment. For instance, the tissue may be treated as part of a prophylactic oral care regimen. The EPAC(s) can be incorporated into an oral care composition or device, such as a toothpaste, a tooth gel, a mouthwash or rinse, or a dental floss, that is employed in such a regimen and will be used regularly, preferably at least once per day, more preferably two or three times per day. In another alternative, the EPAC(s) may be contained in a separate oral care composition or device which will be used separately from other compositions and devices employed in the prophylactic oral care regimen. For instance, the EPAC(s) can be incorporated into a mouthwash or rinse, a gum, a lozenge or a chewable tablet, which would be used regularly, preferably at least once per day, more preferably at least two or three times per day.

Tissues may also be treated prophylactically in connection with a variety of dental procedures, including surgeries and tooth extractions. For instance, the tissue(s) on which surgery is being performed, those tissues near the area where the surgery is being performed or, for ease of treatment, all or substantially of the tissues of the mouth, can be treated prior to surgery, during surgery, after the surgery, or combinations thereof. Similarly for a tooth extraction, the tissue(s) surrounding the tooth which is to be extracted, adjacent tissues or, for ease of treatment, all or substantially of the tissues of the mouth, can be treated prior to tooth extraction, during the tooth extraction, after the tooth extraction, or combinations thereof. For instance, the mouth could be rinsed prior to surgery or tooth extraction with a solution comprising the EPAC(s), the wound(s) caused by the surgery or tooth extraction could be closed with sutures having the EPAC(s) incorporated into them, and/or the mouth could be rinsed immediately after the surgery or tooth extraction, and/or at intervals thereafter, with a solution comprising the EPAC(s). Finally, as described above, tissues may be treated prophylactically in connection with the whitening of the teeth of an animal.

An EPAC or EPACs of the invention can also be used to treat a disease or condition of a tissue of an animal's mouth that is mediated by increased phosphorylation. Specific diseases and conditions treatable according to the invention include inflammation and inflammatory diseases and conditions, such as inflammation of the periodontal tissue, gingivitis, periodontitis, infections (bacterial infections, viral infections, yeast infections and fungal infections), ulcers, cold sores, canker sores and inflammation accompanying surgery or tooth extraction. The treatment of other diseases and conditions of the mouth, such as cancer, is more typically performed by, or under the supervision of, a medical doctor, rather than a dentist. Accordingly, the treatment of these disease and conditions was dealt with above in the discussion of therapeutic methods and pharmaceutical products. However, the use of the oral care products of the invention and the use of the pharmaceutical products of the invention together in the treatment of these types of diseases and conditions of the mouth should be beneficial.

It is understood by those skilled in the art that the dosage amount of the EPAC(s) needed to treat a tissue of an animal's mouth will vary with the particular EPAC employed, whether the treatment is prophylactic or for the treatment of a disease or condition, the identity of the disease or condition to be treated, the severity of the disease or condition, the type of oral care composition used, the duration of the treatment, the identify of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. It is expected that usage of oral care compositions comprising from about 0.000001% to about 20% of an EPAC or EPACs one or more times per day will provide effective daily dosages. However, the actual daily dosage to be employed, the number of treatments per day, and the length of treatment will be determined by an attending dentist or veterinarian within the scope of sound medical judgment.

The invention also provides a kit comprising an oral care product according to the invention. In the case where the oral care product is an oral care composition, the kit may also include an applicator for applying the oral care composition to a tissue of an animal's mouth, such as a swab, a stick, a plastic paddle, a dropper, a syringe, a strip (such as that described in U.S. Pat. Nos. 5,891,453 and 6,419,906) or a dental tray or appliance (such as those shown in U.S. Pat. Nos. 5,863,202 and 5,980,249 and EP application 752833) which allows for immersion of the teeth and, optionally, the periodontal tissue in, e.g., a gel or solution. The kit could also include a cup, vial or other device for dispensing and/or measuring the amount of the oral care composition of the invention needed for the intended use. Of course, the kits could include both an oral care composition and an oral care device according to the invention. In addition to an oral care composition and/or device of the invention, the kits could also comprise another type of oral care composition or device, such as a tooth whitening composition, strips comprising a tooth whitening agent, applicators for applying oral care compositions, etc. Kits according to the invention will also include instructions for using the kit and/or the oral care product of the invention and may include any other desired items.

E. Personal Care Products and Methods

The EPAC(s) of the invention may also be administered to an animal as personal care products. Personal care products include personal care compositions and personal care devices.

Personal care compositions and devices of the invention include compositions and devices intended for use by consumers and patients and compositions and devices intended for use by professionals (e.g., dermatologists, beauty salons and spas). Preferred EPACs for use in the personal care products of the invention are phosvitins and caseins which are at least partially dephosphorylated.

Personal care compositions include cosmetics, skin creams and lotions, face and body moisturizers, suntan creams and lotions, oils, washes, rinses, solutions, eye drops, emulsions, liquids, gels, ointments, sprays, powders, deodorants, shampoos, scalp treatment compositions, lip glosses, lip balms, anti-acne preparations, analgesics, etc.

The personal care compositions of the invention comprise an EPAC or EPACs and a pharmaceutically-acceptable carrier. The personal care compositions may also comprise one or more other acceptable ingredients, including other active compounds and/or other ingredients conventionally used in personal care compositions. Each carrier and ingredient must be "acceptable" in the sense of being compatible with the EPAC(s) and any other ingredients of the composition and not being injurious to the animal. Suitable ingredients for use in personal care compositions and methods of making and using personal care compositions are well known in the art.

A wide variety of carriers suitable for use in skin care compositions are well known in the art. For example, emulsion carriers (including oil-in-water, water-in-oil, water-in-oil-in-water and oil-in-water-in-silicone emulsions) can be used. These emulsions can cover a broad range of viscosities (e.g., from about 100 centipoise (cps) to about 200,000 cps). Other suitable carriers include: anhydrous liquid solvents, such as oils, alcohols and silicones (e.g., mineral oil, ethanol, isopropanol, dimethicone, cyclomethicone and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts and the like). The carrier preferably comprises from about 50% to about 99% by weight of the skin care compositions, more preferably from about 75% to about 99%, most preferably from about 85% to about 95%.

A wide variety of carriers suitable for use in hair care compositions are also well known in the art. For instance, water, alcohols (e.g., methanol, ethanol and isopropanol) and mixtures thereof can be used. The carriers can also comprise a wide variety of additional materials including acetone, hydrocarbons (e.g., isobutane, hexane, decene), linalool, esters (e.g., ethyl acetate and dibutyl phthalate), volatile silicone derivatives (e.g., siloxanes, such as phenyl pentamethyl disiloxane, methoxypropyl heptamethyl cyclotetrasiloxane, chloropropyl pentamethyl disiloxane, hydroypropyl pentamethyl disiloxane, octamethyl cyclotetrasiloxane, decamethyl cyclopentasiloxane, cyclomethicone and dimethicone), and mixtures thereof. Hair care products having a low viscosity may also utilize an emulsifying agent (preferably at a level of from about 0.01% to about 7.5% by weight of the composition). The carrier will comprise from about 0.5% to about 99.5% by weight of the hair care compositions, preferably from about 5.0% to about 99.5%, more preferably from about 10.0% to about 98.0%.

In addition to the EPAC(s) and the carrier, the personal care compositions of the invention can comprise a wide variety of additional ingredients. These additional ingredients include pharmaceutically active ingredients (e.g., anti-acne actives, analgesic actives, antipruritic actives, anesthetic actives and antimicrobial actives), other active ingredients (e.g., sunscreening actives, sunless tanning actives, skin bleaching actives, anti-dandruff actives, antiperspirant actives and deodorant actives), conditioners, humectants, moisturizers, surfactants, thickeners, emollients and other ingredients commonly used in personal care compositions.

As noted above, the pharmaceutically active ingredients that can be included in the personal care compositions of the invention in addition to the EPACs include anti-acne actives, analgesic actives, antipruritic actives, anesthetic actives and antimicrobial actives. Amounts of these ingredients to include in the compositions are known in the art or can be determined empirically. Suitable dosage amounts will vary with, e.g., the specific active ingredient, the ability of the compositions to penetrate the active through the skin, the amount of composition to be applied, the particular condition being treated, the age and physical condition of the animal being treated, the severity of the condition, the duration of the treatment, the nature of concurrent therapy and like factors.

Anti-acne actives include the keratolytics (such as salicylic acid, sulfur, lactic acid, glycolic, pyruvic acid, urea, resorcinol and N-acetylcysteine), retinoids (such as retinoic acid and its derviatives), antibiotics and antimicrobials (such as benzoyl peroxide, octopirox, erythromycin, zinc, tetracycline, triclosan, azelaic acid and its derivaties, phenoxy ethanol, phenoxy propanol, ethylacetate, clindamycin and meclocycline), sebostats (such as flavinoids), alpha and beta hydroxy acids, and bile salts (such as scymnol sulfate and its derivatives, deoxycholate and cholate).

Analgesic actives include salicylic acid derivatives (such as methyl salicylate), species and derivatives of the genus *capsicum* (such as capsaicin), steroids (such as hydrocortisone) and non-steroidal anti-inflammatory drugs (NSAIDS). The NSAIDS can be selected from the following categories: propionic acid derivatives (aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid), acetic acid derivatives, fenamic acid derivatives, biphenylcarboxylic acid derivatives and oxicams.

Antipruritic actives include the pharmaceutically-acceptable salts of methdilizine and trimeprazine.

Anesthetic actives include the pharmaceutically-acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Antimicrobial (antibacterial, antifungal, antiprotozoal and antiviral) actives include pharmaceutically-acceptable salts of β-lactams, quinolones, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole, amanfadine, octopirox, parachlorometa xylenol, nystatin, tolnaftate and clotrimazole.

Sunscreening agents include 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zine oxide, silica, iron oxide, and mixtures thereof. Additional sunscreening agents include those having, in a single molecule, two distinct chromophore moities which exhibit different ultraviolet radiation absorption spectra (one absorbs predominantly in the UVA range and one absorbs predominantly in the UVB range), such as 4-N,N-(2-ethylhexyl)methylaminobenzoic acid ester of 2,4-dihydroxybenzophenone, 4-N,N-(2-ethylhexyl)methylaminobenzoic acid ester of 4-hydroxydibenzoylmethane, 4-N,N-(2-ethylhexyl)methylaminobenzoic acid ester of 2-hydroxy-4-(2-hydroxyethoxy)benzophenone, 4-N,N-(2-ethylhexyl)methylaminobenzoic acid ester of 4-(2-hydroxyethoxy)dibenzoylmethane, and mixtures thereof. See also PCT application WO 03/013468 which describes additional suitable sunscreening agents. Generally, the sunscreens will comprise from about 0.5% to about 20% by weight of the compositions. Exact amounts will vary depending upon the sunscreen chosen and the desired Sun Protection Factor (SPF), SPF is a commonly used measure of photoprotection of a sunscreen against erythema. See *Federal Register*, Volume 43, No. 166, pages 38206-38269, Aug. 25, 1978.

Sunless tanning actives include dihydroxyacetone, glyceraldehyde, indoles and their derivatives, and the like.

Skin bleaching actives include hydroquinone, ascorbic acid, kojic acid and sodium metabisulfite.

Anti-dandruff actives include zinc pyrithione, octopirox, selenium disulfide, sulfur, coal tar and the like.

Antiperspirant actives include astringent metallic salts, such as the inorganic and organic salts of aluminum, zirconium and zinc, as well as mixtures thereof.

Deodorant actives include bacteriostats (e.g., 2,2'-methylenebis(3,4,6-trichlorophenol), 2,4,4'-trichloro-2'-hydroxy (diphenyl ether) (also known as triclosan), zinc phenolsulfonate, 2,2'-thiobis(4,6-dichlorophenol), p-chloro-m-xylenol, dichloro-m-xylenol, sodium N-lauroyl sarcosine, sodium N-palmitoyl sarcosine, lauroyl sarcosine, N-myristoyl glycine, potassium N-lauroyl sarcosine, aluminum chlorhydroxy lactate, and the like).

Conditioning agents useful in the compositions, especially the hair care compositions, include hydrocarbons, silicone fluids and cationic materials. The hydrocarbons can be either straight or branched-chain and can contain from about 10 to about 16 carbon atoms. Examples of suitable hydrocarbons include decane, dodecane, tetradecane, tridecane and mixtures thereof. Silicone conditioning agents include cyclic or linear polydimethylsiloxanes, phenyl and alkyl phenyl silicones, and silicone copolyols. Cationic conditioning agents include quaternary ammonium salts (e.g., dialkyl dimethyl ammonium salts wherein the alkyl groups have 12-22 carbon atoms (such as ditallow dimethyl ammonium chloride, ditallow dimethyl ammonium methyl sulfate, dihexadecyl dimethyl ammonium chloride and di(hydrogenated tallow) ammonium chloride) and dicationics (such as tallow propane diammonium dichloride)), quaternary imidazolinium salts (e.g., imidazolinium salts containing alkyl groups containing 12-22 carbon atoms (such as 1-methyl-1[(stearoylamide) ethyl]-2-heptadecyl-4,5-dihydroimidazolinium chloride, 1-methyl-1[(palmitoylamide)ethyl]-2-octadecyl-4,5-dihydroimidazolinium chloride and 1-methyl-1[(tallowamide) ethyl]-2-tallow-imidazolinium methyl sulfate)) and the salts of fatty amines (e.g., stearylamine hydrochloride, soyamine hydrochloride and stearylamine formate).

Humectants and moisturizing agents include urea, guanidine, glycolic acid and glycolate salts (e.g., ammonium and quaternary alkyl ammonium), lactic acid and lactate salts (e.g, ammonium and quaternary alkyl ammonium), aloe vera in any of its variety of forms (e.g., aloe vera gel), polyhydroxy alcohols (e.g, sorbitol, glycerol, hexanetriol, propylene glycol, butylene glycol, hexylene glycol and the like)), polyethylene glycols, sugars and starches, sugar and starch derivatives (e.g., alkoxylated glucose), hyaluronic acid, lactamide monoethanolamine, acetamide monoethanolamine, and mixtures thereof. These agents will generally be present at a level of from about 0.1% to about 20% of the weight of the compositions.

Surfactants useful in the compositions include anionic, nonionic, cationic, zwitterionic and amphoteric surfactants. Suitable anionic surfactants include long chain sulfates, sulfonates, isethionates, carboxylates, taurates, and sulfosuccinates, such as alkyl glyceryl ether sulfonate, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinsate, lauryl sarcosine, cocoyl sarcosine, ammonium cocoyl sulfate, ammonium lauroyl sulfate, sodium cocoyl sulfate, sodium lauroyl suflate, potassium cocoyl sulfate, potassium lauryl sulfate, triethanolamine lauryl sulfate, monoethanolamine cocoyl sulfate, monoethanolamine lauryl sulfate, sodium tridecyl benzene sulfonate and sodium dodecyl benzene sulfonate. For cationic surfactants, see U.S. Pat. No. 5,916,548 and the references cited therein. Nonionic surfactants include the compounds produced by condensation of alkylene oxide groups (hydrophilic in nature) with an organic hydrophobic compound, which may be aliphatic or alkyl aromatic in nature. Amphoteric and zwitterionic surfactants include betaines, such as amidocarboxybetaines, alkyl betaines, amidopropyl betaines, amidopropyl sultaines and sulfobetaines. Additional amphoteric and zwitterionic surfactants include derivatives of aliphatic quaternary ammonium and sulfonium compounds, in which the aliphatic radicals can be straight or branched chain and wherein one of the aliphatic substituents contains from about 8-18 carbon atoms and one contains an anionic water-solubilizing group (e.g., carboxy, sulfonate or sulfate). Further amphoteric and zwitterionic surfactants include derivatives of aliphatic secondary and tertiary amines, in which the aliphatic radicals can be straight or branched chain and wherein one of the aliphatic substituents contains from about 8-18 carbon atoms and one contains an anionic water-solubilizing group (e.g., carboxy, sulfonate or sulfate), such as sodium 3-dodecyl-aminopropionate, sodium 3-dodecylamino propane sulfonate and N-alkyl taurines. The surfactant or mixture of surfactants will generally be present at a level of from about 0.2% to about 30% of the weight of the compositions.

Thickeners include carboxylic acid polymers (described in U.S. Pat. No. 5,916,548, the complete disclosure of which is incorporated herein by reference). These crosslinked polymers contain one or more monomers derived from acrylic acid, substituted acrylic acids and salts and esters of these acrylic acids and the substituted acrylic acids, wherein the crosslinking agent contains two or more carbon-carbon double bonds and is derived from a polyhydric alcohol. Specific examples of such polymers are the carbomers, which are homopolymers of acrylic acid crosslinked with allyl ethers of sucrose or pentaerytritol (available as the Carbopol® 900 series from B.F. Goodrich), and copolymers of $C_{10-30}$ alkyl acrylates with one or more monomers of acrylic acid, methacrylic acid or one of their short chain ($C_{1-4}$ alcohol) esters, wherein the crosslinking agent is an allyl ether of sucrose or pentaerytritol (also known as acrylates/C10-30 alkyl acrylate crosspolymers and available as Carbopol® 1342, Pemulen TR-1 and Pemulen TR-2 from B.F. Goodrich). Other thickeners include xanthan gum, guar gum, carboxymethyl cellulose, hydroxymethyl cellulose, hydroxyethyl cellulose, alkyl modified hydroxyalkyl celluloses (e.g, long chain alkyl modified hydroxyethyl celluloses, such as cetyl hydroxyethyl cellulose) and magnesium aluminum silicate. These thickeners will generally be present at a level of from about 0.025% to about 1% of the weight of the compositions.

Emulsifiers suitable for use in personal care compositions can be any of a wide variety of nonionic, cationic, anionic and zwitterionic emulsifiers. Examples of suitable emulsifiers include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, fatty acid amides, acyl lactylates, soaps, and mixtures thereof. Specific suitable emulsifiers include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, Polysorbate 60, glyceryl stearate, PEG-100 stearate and mixtures thereof. The emulsifiers will generally be present at a level of from about 0.1% to about 10% of the weight of the compositions.

Emollients include volatile and nonvolatile silicone oils, highly branched hydrocarbons and nonpolar carboxylic acid and alcohol esters, and mixtures thereof. The emollients will generally be present at a level of from about 1% to about 50% of the weight of the compositions.

A variety of additional ingredients can be included in the personal care compositions. These additional ingredients include vitamins and derivatives thereof (e.g., ascorbic acid, vitamin E tocopheryl acetate, retinoic acid, retinol, retinoids and the like), polyquatemium and mineral oil, resins, gums, polymers for aiding in the film-forming properties and substantivity of the composition (such as a copolymer of eicosene and vinyl pyrrolidone), suspending agents (e.g., ethylene glycol distearate and the like), preservatives, skin penetration aids, antioxidants, chelators, sequestrants and aesthetic components (e.g., fragrances, colorings, essential oils, skin sensates, astringents and skin soothing agents; specific examples of such aesthetic components include panthenol and its derivatives, pantothenic acid and its derivatives, clove oil, menthol, camphor, eucalyptus oil, eugenol, menthyl lactate, witch hazel distillate, allantoin and bisabalol).

It will be appreciated that a wide variety of different personal care compositions can be prepared utilizing the above described ingredients and other ingredients known in the art or which will be developed. It is within the skill in the art to chose appropriate ingredients and combinations of ingredients and to determine an effective amount of the EPAC(s) of the invention to include in a particular personal care composition.

The invention also provides personal care devices. Personal care devices include surgical materials (such as sutures and sponges), bandages, sponges, cloths, swabs, pads and wipes. The personal care devices of the invention will have an EPAC or EPACs adhered to, absorbed into, adsorbed onto, bound to, attached to, entrapped in, impregnated in, coated onto or otherwise incorporated into, them. For instance, a device can be soaked in a solution of an EPAC or EPACs, followed by removal of the solvent, to adhere, absorb, adsorb, bind, attach, entrap, impregnate, coat the device with the EPAC(s). See, e.g., the description above of the preparation of oral care devices.

The invention also provides a method of inhibiting increased phosphorylation in an animal's skin. The method comprises contacting the skin with an effective amount of an EPAC or EPACs. For instance, the skin may be contacted with a personal care composition comprising the EPAC(s). Methods of contacting the skin with personal care compositions are well known in the art. Suitable methods include washing the skin with a cleaning solution, rinsing the skin with a rinse, applying a solution, gel, cream, lotion or ointment on the skin (with or without the use of an applicator), washing the hair with a shampoo that contacts the scalp, and many other means of topical application. Suitable applicators for applying personal care compositions include a cotton ball, a gauze pad, a wipe, a cloth, a swab, a dropper, a syringe or a finger. In addition, the skin may be contacted with a personal care device comprising the EPAC(s). Methods of contacting the skin with personal care devices are well known in the art. For instance, sutures can be used to close a surgical wound, a wipe or pad impregnated with the EPAC(s) can be used to clean the skin, a bandage comprising the EPACs can be applied to the skin, etc.

The treatment of the skin can be prophylactic treatment. For instance, the skin may be treated as part of a prophylactic skin care regimen. The EPAC(s) can be incorporated into a personal care composition or device that is employed in such a regimen or the EPAC(s) may be contained in a separate personal care composition or device which will be used separately from other compositions and devices employed in the prophylactic skin care regimen. The prophylactic regimen is performed regularly (e.g., monthly or daily).

Skin may also be treated prophylactically in connection with a variety of dermatological procedures, including surgeries, dermabrasions and chemical peels. For instance, the area of skin on which surgery is to be performed can be treated prior to surgery, during surgery, after the surgery, or combinations thereof. For instance, the skin could be rinsed prior to surgery with a solution comprising the EPAC(s), the wound(s) caused by the surgery could be closed with sutures having the EPAC(s) incorporated into them, and/or the skin could be rinsed immediately after the surgery, and/or at intervals thereafter, with a solution comprising the EPAC(s).

A personal care product comprising an EPAC or EPACs of the invention can also be used to treat a disease or condition of the skin that is mediated by increased phosphorylation. Specific diseases and conditions treatable according to the invention are described above in the discussion of therapeutic methods and pharmaceutical compositions. It will be appreciated that diseases and conditions of the skin can be treated with a pharmaceutical composition and/or a personal care composition or device.

It is understood by those skilled in the art that the dosage amount of the EPAC(s) needed to treat an animal's skin using a personal care product will vary with the particular EPAC employed, whether the treatment is prophylactic or for the treatment of a disease or condition, the identity of the disease or condition to be treated, the severity of the disease or condition, the type of personal care composition or device used, the duration of the treatment, the identify of any other drugs being administered to the animal, the age, size and species of the animal, and like factors.

The invention also provides a kit comprising a personal care product according to the invention. In the case where the personal care product is a personal care composition, the kit may also include an applicator for applying the personal care composition, such as a swab, cotton balls, wipes, pads, a plastic paddle, a squeeze bottle, a pump bottle, a dropper, or a syringe. The kit could also include a cup, vial or other device for dispensing and/or measuring the amount of the personal care composition of the invention needed for the intended use. Of course, the kits could include both a personal care composition and a personal care device according to the invention. In addition to a personal care composition and/or device of the invention, the kits could also comprise another type of personal care composition or device. Kits according to the invention will also include instructions for using the kit and/or the personal care product of the invention and may include any other desired items.

It is to be noted that "a" or "an" entity refers to one or more of that entity. For example, "a tissue" refers to one or more tissues.

EXAMPLES

Example 1

Inhibition of IL-8 by Dephosphorylated Phosvitin

Phosvitin was extracted from the yolks of chicken eggs as described by Losso and Nakai, in *Egg Uses And Processing Technologies: New Developments*, pages 150-157 (Sim and Nakai, eds., Cab International, Oxon, UK, 1994). It was dephosphorylated as described by Reimerdes and Klostermeyer, in *Methods in Enzymology*, Volume 45, pages 26-28 (1976). This phosvitin preparation was estimated to be about 20-50% dephosphorylated.

Chicken phosvitin was also purchased from Sigma Chemical Co., St. Louis, Mo., as was bovine serum albumin (BSA; ELIS grade=low fatty acid and IgG). Each was used as received from the manufacturer without dephosphorylation.

Jurkat cells (American Type Culture Collection (ATCC), Rockville, Md.) were cultured ($1 \times 10^6$ cells per 0.5 ml culture) in IMDM culture medium (ATCC) containing insulin transferrin selenite solution (ITSS; Sigma) with and without phosvitin or BSA at 37° C., 5% $CO_2$, for 30 minutes. Then, phorbol-12-myristate-13-acetate (PMA; 100 mg/ml; Sigma) and ionomycin (100 mg/ml; Sigma) were added to stimulate the cells, and the cells were further cultured at 37° C., 5% $CO_2$, for 24 hours.

Cell culture supernatants were analyzed for IL-8 content by ELISA. The IL-8 ELISA was performed as follows. Antihuman IL-8 antibody (Pierce Endogen, Rockford, Ill.; catalogue number M801-E, lot number CK41959) was diluted to 1 μg/ml in phosphate buffered saline, pH 7.2-7.4, and 100 μl of the diluted antibody was added to each well of Nunc Maxisorb ELISA strip plates. The plates were incubated overnight at room temperature. The liquid was aspirated from the wells, and the plates were blotted on a paper towel. Then, 200 μl of assay buffer (phosphate buffered saline, pH 7.2-7.4, containing 4% BSA) were added to each well, and the plates were incubated for 1 hour at room temperature. The liquid was aspirated from the wells, and the wells were washed 3 times with wash buffer (50 mM Tris, 0.2% Tween-20, pH 7.9-8.1) and were then blotted on a paper towel. Standards and supernatant samples (50 μl/well; standards were diluted in assay buffer) were added to the wells, and the plates were incubated for 1 hour at room temperature with gentle shaking. The liquid was aspirated, the wells were washed 3 times with wash buffer, and the plates were then blotted on a paper towel. Then, 100 μl of biotin-labeled anti-human IL-8 (Pierce Endogen, Rockford, Ill.; catalogue number M802-E, lot number CE49513), diluted to 60 ng/ml in assay buffer, were added to each well. The plates were incubated for 1 hour at room temperature, the liquid was aspirated, the wells were washed 3 times with wash buffer, and the plates were blotted on a paper towel. Then, 100 μl of HRP-conjugated streptavidin (Pierce Endogen, Rockford, Ill.; catalogue number N100) in assay buffer, were added to each well. The plates were incubated for 30 minutes at room temperature, the liquid was aspirated, the wells were washed 3 times with wash buffer, and the plates were blotted on a paper towel. Finally, 100 μl of TMB substrate solution (Pierce Endogen, Rockford, Ill.; catalogue number N301) were added to each well. The plates were incubated for 30 minutes at room temperature. The reaction was stopped by adding 100 μl/well of 0.18 M $H_2SO_4$. The optical densities at 450 mu and 530 nm were read on an ELISA plate reader and the difference (OD 450-OD 530) calculated.

The results are shown in Table 1. As can be seen, it was found that the phosvitin isolated from chicken egg yolks inhibited IL-8 release as compared to the positive control in a dose-dependent fashion. The BSA and phosvitin from Sigma did not significantly inhibit the release of IL-8.

TABLE 1

| Sample | IL-8 (pg/ml) | Percent Inhibition Of IL-8 Release |
|---|---|---|
| Negative control (no PMA, no ionomycin, no BSA, no phosvitin) | 0.0 | — |
| Positive control (PMA and ionomycin; no BSA or phosvitin) | 1119.2 | — |
| 0.1 mg/ml chicken egg yolk phosvitin (dephosphorylated) and PMA and ionomycin | 1024.7 | 6.4% |
| 0.5 mg/ml chicken egg yolk phosvitin (dephosphoryalted) and PMA and ionomycin | 830.4 | 25.8% |
| 1.0 mg/ml chicken egg yolk phosvitin (dephosphorylated) and PMA and ionomycin | 686.9 | 38.6% |
| 1.0 mg/ml Sigma phosvitin (untreated) and PMA and ionomycin | 1153.6 | 0% |
| 1.0 mg/ml Sigma BSA (untreated) and PMA and ionomycin | 1048.1 | 6.3% |

Example 2

Use of Dephosphorylated Phosvitin to Treat Inflammation

Chicken phosvitin (Sigma) in distilled water (0.5 g/100 ml) was dephosphorylated by adding 0.4 N NaOH at 37° C. for 3 hours as described in Jiang et al., *J. Agric. Food Chem.*, 48:990-994 (2000). After dephosphorylation, the pH of the phosvitin solution was adjusted to 7.8 with 0.1 N HCl. This phosvitin preparation was found to be 73% dephosphorylated using a gallium column.

A cream was prepared by mixing the dephosphorylated phosvitin with 100 ml Eucerin cream (Beiersdorf Inc., Wilton, Conn.) to give a final phosvitin concentration of about 0.25%.

A human volunteer with a chronic skin lesion (etiology unknown) applied the phosvitin cream to the lesion twice per day for two days. The lesion disappeared completely after this treatment.

Another human volunteer with chronic skin lesions (diagnosed as atopic dermatitis) applied the phosvitin cream to a lesion on the back twice per day for one week. The treated lesion completely disappeared. Other lesions on this same volunteer that were not treated with the phosvitin cream were unchanged.

A third human volunteer with a chronic skin lesion (diagnosed as chronic eczema) applied the phosvitin cream to the lesion twice per day for one week. The lesion completely disappeared after the treatment. This volunteer's lesion has been resistant to all previous prescription treatments, including topical steroids.

A fourth human volunteer with a chronic skin lesion on the top of the head (diagnosed by biopsy to be chronic solar keratosis/elastosis) applied the phosvitin cream to the lesion twice per day for one week. The lesion almost completely disappeared. This volunteer's lesion has been chronic for over 25 years and had not responded previously to any dermatological treatment, including topical steroids, antibiotics, antifungals, silver nitrate and freezing with liquid nitrogen.

A fifth human volunteer with a psoriasis lesion on the ankle applied the phosvitin cream to the lesion twice per day for one week. The lesion completely disappeared after this treatment.

Example 3

Inhibition of IL-8 By Unphosphorylated Kinase Substrates

Casein kinase I substrate (sequence Arg Arg Lys Asp Leu His Asp Asp Glu Glu Asp Glu Ala Met Ser Ile Thr Ala [SEQ ID NO:3]) and casein kinase II substrate (sequence Arg Arg Arg Ala Asp Asp Ser Asp [SEQ ID NO:4]) were purchased from Sigma-Aldrich, St. Louis, Mo. Each was used as received from the manufacturer since they were unphosphorylated.

Jurkat cells (American Type Culture Collection (ATCC), Rockville, Md.) were cultured ($2\times10^6$ cells per 1.0 ml culture) in IMDM culture medium (ATCC) containing insulin transferrin selenite solution (ITSS; Sigma) with and without each of the casein kinase substrates (50 µg/ml and 100 µg/ml) at 37° C., 10% $CO_2$, for 15 minutes. Then, phorbol-12-myristate-13-acetate (PMA; 100 mg/ml; Sigma) and ionomycin (100 mg/ml; Sigma) were added to stimulate the cells, and the cells were further cultured at 37° C., 5% $CO_2$, for 24 hours.

Cell culture supernatants were analyzed for IL-8 content by ELISA as described in Example 1. The results are shown in FIG. 1. As can be seen, it was found that the both of the casein kinase substrates inhibited IL-8 release as compared to the positive control in a dose-dependent fashion.

I claim:

1. A method to reduce the severity of eczema or a dermatitis mediated by increased phosphorylation in an animal comprising administering an effective amount of a partially dephosphorylated phosphate-acceptor compound (PAC) to said animal in need thereof, wherein the PAC is a phosvitin which is at least 10% to 70% dephosphorylated.

2. The method of claim 1 wherein the phosvitin is chicken phosvitin.

3. The method of claim 2 wherein the phosvitin fragment thereof is at least about 90% dephosphorylated.

4. The method of claim 1 wherein the phosvitin fragment thereof is at least about 90% dephosphorylated.

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Homo sapiens

<400> SEQUENCE: 1

Lys Cys Ala Ser
1

<210> SEQ ID NO 2
<211> LENGTH: 6
<212> TYPE: PRT
<213> ORGANISM: Homo sapiens

<400> SEQUENCE: 2

Lys Ala Ser Ser Ala Lys
1               5

<210> SEQ ID NO 3
<211> LENGTH: 18
<212> TYPE: PRT
<213> ORGANISM: Homo sapiens

<400> SEQUENCE: 3

Arg Arg Lys Asp Leu His Asp Asp Glu Glu Asp Glu Ala Met Ser Ile
1               5                   10                  15

Thr Ala

<210> SEQ ID NO 4
<211> LENGTH: 8
```

-continued

```
<212> TYPE: PRT
<213> ORGANISM: Homo sapiens

<400> SEQUENCE: 4

Arg Arg Arg Ala Asp Asp Ser Asp
1               5
```